(12) United States Patent
Nekozuka et al.

(10) Patent No.: US 6,190,618 B1
(45) Date of Patent: Feb. 20, 2001

(54) GARBAGE PROCESSING APPARATUS HAVING DEODORIZING UNIT

(75) Inventors: Tadaaki Nekozuka; Kiyoshi Fukushima; Hirohide Nakao; Tomio Terayama; Akihiro Shirata; Sinichiro Fujita; Kenichi Ueda; Masami Hatayama; Hiroshi Ohdate, all of Ebina (JP)

(73) Assignee: Jidosha Buhin Kogyo Co., Ltd, Kanagawa (JP)

(*) Notice: Under 35 U.S.C. 154(b), the term of this patent shall be extended for 0 days.

(21) Appl. No.: 09/388,324

(22) Filed: Sep. 1, 1999

Related U.S. Application Data

(62) Division of application No. 08/859,562, filed on May 20, 1997, now Pat. No. 5,980,823.

(30) Foreign Application Priority Data

| May 27, 1996 | (JP) | 8-132461 |
| May 27, 1996 | (JP) | 8-132462 |
| Oct. 28, 1996 | (JP) | 8-285222 |
| Nov. 5, 1996 | (JP) | 8-292921 |

(51) Int. Cl.[7] .................................................. G05D 23/00
(52) U.S. Cl. ............................ 422/108; 241/23; 241/65; 241/DIG. 38; 422/4; 422/5; 422/109; 422/307; 422/308; 422/309
(58) Field of Search .......................... 422/4, 5, 307, 422/308, 309, 120, 108, 109; 241/23, 65, DIG. 38

(56) References Cited

U.S. PATENT DOCUMENTS

| 5,362,443 | 11/1994 | Tanaka et al. ........................ 422/26 |
| 5,364,602 | 11/1994 | Leduc .................................. 422/307 |
| 5,439,643 | 8/1995 | Liebert ............................ 422/307 X |
| 5,456,881 | 10/1995 | Bandel et al. .................. 422/309 X |
| 5,482,685 | 1/1996 | Fujita et al. .................... 422/307 X |
| 5,487,873 | 1/1996 | Bridges et al. ................ 422/307 X |
| 5,527,516 | * 6/1996 | Yamamoto et al. ............... 422/26 X |
| 5,577,675 | 11/1996 | Ishikawa ............................. 241/65 |
| 5,634,600 | 6/1997 | Kubota et al. ............... 241/DIG. 38 |
| 5,980,832 | * 11/1999 | Nekozuka et al. ..................... 422/4 |

FOREIGN PATENT DOCUMENTS

| 5-24601 | 2/1993 | (JP) | B65F/1/14 |
| 5-39972 | 2/1993 | (JP) | F25D/1/00 |
| 6-22637 | 8/1994 | (JP) | B09B/3/00 |

* cited by examiner

*Primary Examiner*—Krisanne Thornton
(74) *Attorney, Agent, or Firm*—McCormick, Paulding & Huber LLP

(57) ABSTRACT

A garbage processor has a vessel for receiving garbage, a rotary pulverizer/stirrer for crushing and stirring the garbage in the vessel and a first heater for drying the garbage in the vessel. A steam is generated upon heating and drying of the garbage. An air blower feeds a high pressure an ambient air into the vessel to force the steam out of the vessel. A steam separator is provided for separating the steam into a water and a gas. A second heater is provided downstream of the steam separator for oxidizing the gas emanating from the steam separator to reduce a smell of the gas. The gas is deodorized before it is discharged to the atmosphere.

13 Claims, 23 Drawing Sheets

GARBAGE PROCESSING APPARATUS HAVING DEODORIZING UNIT

CROSS REFERENCE TO RELATED APPLICATION

This application is a divisional application divided from prior application Ser. No. 08/859,562 filed May 20, 1997 now U.S. Pat. No. 5,980,823.

BACKGROUND OF THE INVENTION

1. Field of the Invention

The present invention relates to an apparatus having a heating vessel for heating and drying garbage such as kitchen refuse in the heating vessel so as to reduce a volume of the garbage and more particularly to such an apparatus which also has a device for deodorizing a smell of a steam generated upon heating and drying of the garbage.

2. Description of the Related Art

In recent years, various apparatuses were proposed for processing garbage which contains a lot of moisture such as that disposed from a kitchen of a restaurant by heating and drying the garbage. For example, Japanese Patent Application, Laid-Open Publication No. 6-226237 published Aug. 16, 1994 discloses one of such apparatuses. FIG. 22 of the accompanying drawings illustrates it. This conventional garbage processing apparatus 14 includes a vessel 1 equipped with an oil heater, a rotary cutter 2 provided in the vessel 1, a motor 10 for actuation of the rotary cutter and a lid 3 for the vessel 1 which opens to form an inlet opening 11 for introduction of garbage into the vessel. The garbage thrown into the vessel 1 is crushed, stirred and heated simultaneously in the vessel 1 to vaporize a moisture included in the garbage. Removal of the moisture results in volume reduction of the garbage. The dried garbage having a smaller volume and weight is discharged from the vessel 1. The garbage processing apparatus 14 also includes a compressor 4, a steam separator 5 and a heat exchanger 7 connected in series. The steam generated in the vessel 1 upon the garbage drying/heating operation is drawn out of the vessel 1 by the compressor 4 and compressed before it is introduced to the steam/water separator 5. The steam is then separated into a hot water W and a gas G. The gas G is expelled to the atmosphere and the hot water W is introduced to the heat exchanger 7 protruding into the vessel 1 through a hot water pipe 6. Heat of the hot water W is utilized for heating of the garbage in the vessel 1. The water W then flows out of the vessel 1 through a discharge pipe 8 and a constant pressure regulator 9.

As mentioned earlier, the illustrated conventional garbage processing apparatus 14 employs the compressor 4 for taking the steam out of the vessel 1. The steam generally contains various hot corrosive materials so that the compressor 4 is damaged by the steam and longevity of the compressor 4 is reduced. In addition, the motor 10 for driving the rotary pulverizer/stirrer 2 is situated under the vessel 1 so that the apparatus 14 has a considerable height. As a result, a position of the inlet opening 11 of the vessel 1 becomes high and introduction of the garbage into the inlet 11 becomes troublesome. Furthermore, the gas G generally contains smelly substances so that discharge of the gas G deteriorates the environment.

A conventional manner of operating the garbage processing apparatus also has several problems. For example, if a timer is used to automatically stop the operation of the apparatus 14, an operator determines a time setting according to his experiences or by his guess. In general, the ending time is set to be considerably later than a theoretical time since a seriously worse situation would arise if the garbage processing apparatus stopped prior to completion of heating and drying of the garbage. Therefore, the garbage processing apparatus is wastefully operated for a certain period after the garbage has been heated and dried. This operation method is costly.

Other garbage processing apparatuses are disclosed, for instance, in Japanese Patent Application, Laid-Open Publication Nos. 5-24601 published Feb. 2, 1993 and 5-39972 published Feb. 19, 1993.

SUMMARY OF THE INVENTION

An object of the present invention is to eliminate the above-described problems of the conventional apparatuses.

According to one aspect of the present invention, there is provided a garbage processing apparatus comprising a vessel for receiving garbage, means for crushing and stirring the garbage in the vessel, means for heating and drying the garbage in the vessel, and air compressing means for introducing a fresh air in a pressurized condition into the vessel to discharge a steam generated upon heating and drying of the garbage out of the vessel. The garbage processing apparatus preferably includes a steam separator for separating the steam into a water and a gas. The steam separator may be air cooled. Second heating means is preferably provided downstream of the steam separator for oxidizing the gas emanating from the steam separator so that a smell of the gas is reduced or removed. Downstream of the second heating means, a heat exchanger may be provided for heating the fresh air by the gas heated by the second heating means before the fresh air is introduced into the garbage vessel.

According to this garbage processing apparatus, the air compressing means for feeding the fresh air in a pressurized condition to the vessel is not subjected to the steam containing various corrosive substances since the steam containing hot and corrosive materials is forced out of the vessel by the high pressure ambient air supplied into the vessel. Therefore, the life of the air compressing means is not reduced by the steam. This air compressing means corresponds to the air compressor 4 of the conventional apparatus shown in FIG. 22. If the steam separator is an air-cooled type one, then an installation cost of the apparatus as well as an operation cost is reduced. If the gas separated from the steam by the steam separator is heated and oxidized by the second heating means, the gas is deodorized before it is discharged to the atmosphere. The second heating means can be a small heater so that it is possible to design the apparatus in smaller dimensions. If the heat exchanger is provided downstream of the second heating means, a fresh air of elevated temperature is introduced into the vessel. Therefore, an expense needed for drying the garbage in the vessel is reduced.

A recirculation passage may also be provided for connecting an outlet of the heat exchanger to an inlet of the air compressing means. The gas deodorized in course of oxidization in the second heating means is cooled in the heat exchanger and then caused to flow into the recirculation passage and in turn into the air compressing means. The gas is fed into the vessel together with a fresh air to carry the steam out of the vessel, and the above mentioned process is repeated. Therefore, the smelly gas repeatedly undergoes the deodorizing step.

According to a second aspect of the present invention, there is provided a garbage processing apparatus comprising a vessel having a garbage inlet opening at its top for receiving garbage, means rotatable about its longitudinal axis extending in a height direction of the vessel for crushing and stirring the garbage in the vessel upon rotation of itself, actuation means mounted on a lateral wall of the vessel for actuating the crushing means, means for connecting the stirring means with the actuation means, means for heating and drying the garbage in the vessel, and means for discharging a steam generated upon heating and drying of the garbage out of the vessel. Preferably, a deodorizing unit is also provided on the lateral wall of the vessel for deodorizing the smelly steam discharged from the vessel. The deodorizing unit may be a vertical type. The deodorizing unit may include a steam separator for separating the steam into a gas and a water and a cooling fan for cooling the steam separator using an external air. Preferably, the cooling fan causes the external air to flow along the lateral wall of the vessel.

According to this garbage processing apparatus, the total height of the apparatus can be reduced since the actuation means is not located below the vessel but next to the lateral wall of the vessel. The actuation means corresponds to the motor 10 of the conventional apparatus shown in FIG. 22. The lower the apparatus height, the easier the garbage feeding into the vessel. Further, since the deodorizing unit is a vertical type, a space needed for installation of the apparatus can be also reduced.

According to a third aspect of the present invention, there is provided a garbage processing apparatus comprising a vessel for receiving garbage, means for crushing and stirring the garbage in the vessel, means for heating and drying the garbage in the vessel, means for discharging a steam generated upon heating and drying of the garbage out of the vessel, a temperature sensor for detecting a temperature of a wall of the vessel and a controller for at least deactivating the heating means when the detected wall temperature exceeds a prescribed value.

According to this garbage processing apparatus, the apparatus is automatically stopped when the vessel wall temperature rises to the predetermined value. The inventors found that the vessel wall temperature is indicative of the drying condition of the garbage in the vessel. Relationship between the vessel wall temperature and the garbage drying condition is examined by experiments beforehand, and the garbage processing apparatus is automatically stopped when the vessel wall temperature becomes the preset value. This means that the apparatus is deactivated immediately when the garbage is heated and dried to a desired condition. Therefore, a wasteful operation of the apparatus is avoided. This contributes to running cost reduction as well as energy saving. The prescribed temperature is, for example, 135° C. Instead of detecting the vessel wall temperature, a moisture content or ratio of the garbage in the vessel may be detected and the heating means may be at least deactivated when the detected moisture content drops to a predetermined value. The predetermined moisture content is, for instance, 10 to 15%.

DETAILED DESCRIPTION OF THE INVENTION

Now, preferred embodiments of the present invention will be described with reference to FIGS. 1 through 21 of the accompanying drawings.

Figure 4:
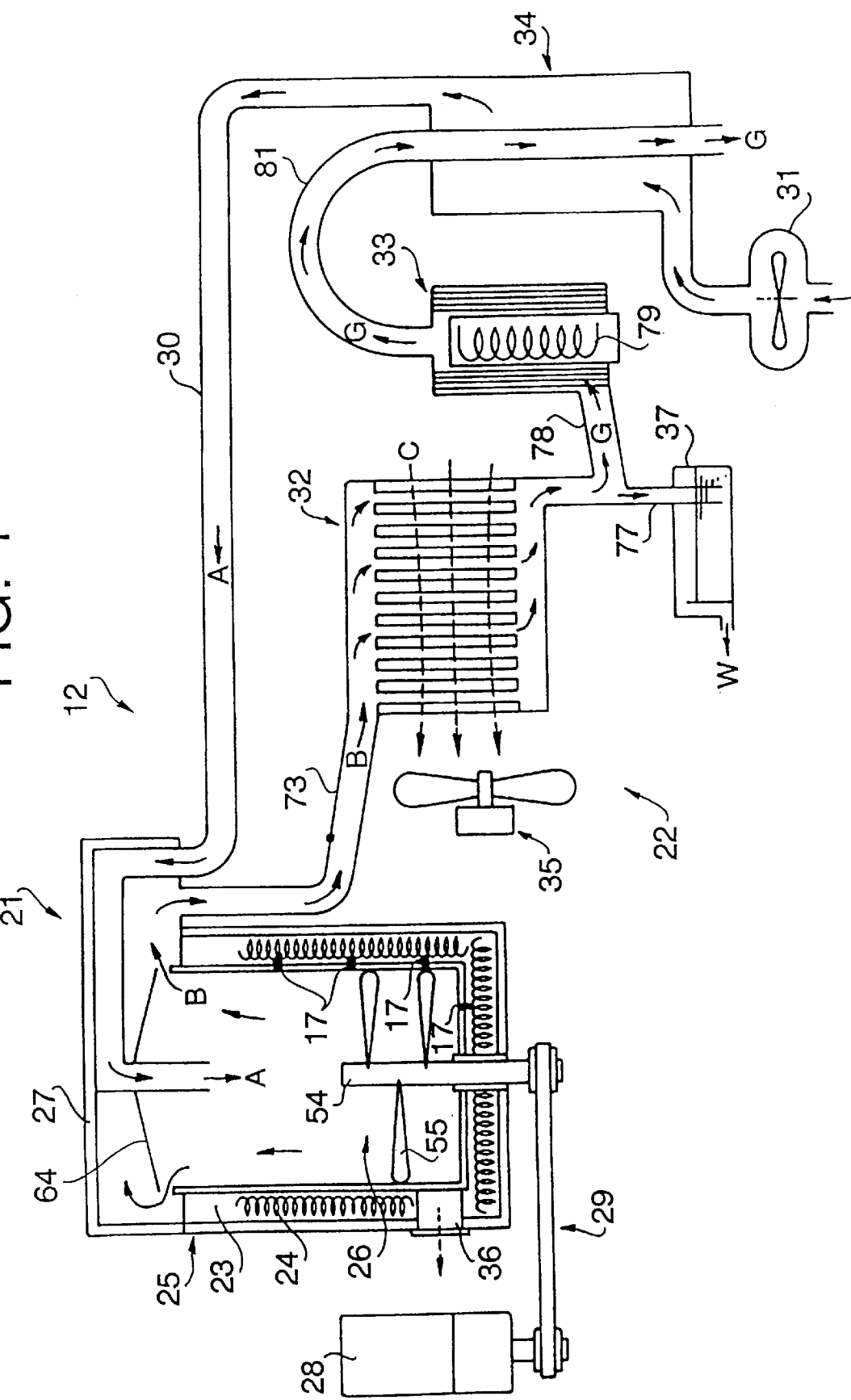
FIG. 4 diagrammatically illustrates an overall construction of the garbage processing apparatus shown in FIG. 1.

First Embodiment:

Referring first to FIG. 4, a basic construction of a garbage processing apparatus 12 according to the present invention will be described. The apparatus 12 includes a heating mechanism 21 for heating and drying garbage and a deodorization mechanism 22 for deodorizing a steam generated upon heating of the garbage before the seam is discharged from the apparatus. The heating mechanism 21 includes a heating vessel unit 25, which is comprised of a vessel 23 and an associated heater 24, and a stirring device 26 placed in the vessel 23 for crushing and stirring the garbage fed into the vessel 23. A lid 27 is provided on the top of the vessel 23 to close a garbage inlet opening. The lid 27 is placed in the illustrated position after the garbage has been thrown into the vessel 23. The vessel 23 is brought into a closed condition as the lid 27 is placed over the top opening of the vessel 23. A plurality of temperature sensors 17 is provided on the heater 24. The stirring device 26 includes a rotating shaft 54 extending along a vertical center axis of the vessel 23 and a plurality of blades 55 radially extending from the rotating shaft 54. The stirring device 26 is connected with a motor 28 by suitable connection means (e.g., combination of sprockets and chains) such that it can rotate in the vessel 23 to crush and stir the garbage. The heating vessel 25 is equipped with an ambient air inlet passage 30. A blower 31 is provided at a position close to an upstream end of the air inlet passage 30 such that a pressurized fresh air A is fed into the vessel 23 through the air passage 30. The high pressure air A forced into the vessel 23 impels a steam B to flow out of the vessel 23. The lid 27 has an inner lid 64 having a shallow conical shape. The outer periphery of the inner lid 64 defines an annular clearance along an upper opening periphery of the vessel 23 such that the steam B can flow out of the vessel 23. The air passage 30 penetrates the inner lid 64 along its center axis downward and terminates in the vessel 23. The steam B is introduced to the deodorization unit 22 from the vessel 23 through a pipe 73 extending from the lid 27. The deodorization unit 22 includes a condenser 32 for separating the steam B into a water W and a gas G, a deodorization heater 33 located downstream of the condenser 32 for heating the gas G so as to oxidize the gas G for deodorization and a heat exchanger 34 for heating the fresh air A introduced to the air passage 30 by the gas G heated by the deodorant heater 33. The heat exchanger 34 also defines part of the air pipe 30. The blower 31 is provided upstream of the heat exchanger 34. A cooling fan 35 is provided for the condenser 32 such that the condenser 32 is cooled by an air C pulled toward the cooling fan 35.

Accordingly, the garbage fed into the heating vessel 23 is crushed/pulverized and stirred by the rotating stirring device 26 and heated by Joule heat derived from the heater 24 surrounding the vessel 23. The heater 24 is heated to about 100 to 125° C. in this particular embodiment. This temperature is detected by the temperature sensors 17. The garbage therefore gradually loses or releases its moisture so that the weight and volume of the garbage decrease. A solid substance (i.e., dried garbage) and the steam B result from this drying operation. The solid substance is pushed out of the vessel 23 from a discharge opening 36 of the vessel 23 formed in a lower portion thereof upon rotation of the blades 55 of the stirring device 26 as indicated by the dashed arrow. Then, the solid substance may be buried in the ground and become a fertilizer or may be burned with other wastes. The steam B generated upon the drying operation in the vessel 23 is forced to the condenser 32 from the vessel 23 through the pipe 73 and is cooled by the condenser 32 so that it becomes the condensed water W and the gas G. An odorant component contained in the steam B partly dissolves in the condensed water W. Therefore, an odorant content in the gas G is smaller than the steam B. The condensed water W is collected into a tank 37 located below the condenser 32 for a while such that a smell does not leak to the outside. The smellless water W is eventually discharged from the garbage processing apparatus. A deodorant agent may be immersed in the tank 37.

The gas G resulting from the gas/liquid separating reaction in the condenser 32 is introduced to the deodorant heater 33 by means of a pipe 78 and heated to a high temperature, e.g., 500 to 600° C. so that the gas G is oxidized. The gas G is substantially deodorized in the course of this oxidization. After that, the smellless gas G flows in a pipe 81 and discharged to the outside. Before the gas G reaches a downstream end of the pipe 81, it is heat exchanged with the fresh air A in the heat exchanger 34 so that the gas G has a lower temperature when it is expelled to the atmosphere. The heater 33 includes a coil 79 extending generally vertically.

In this manner, the blower 31 is provided at the upstream end of the fresh air inlet line 30 to feed the high pressure air A into the vessel 23 and the steam B generated in the vessel 23 is forced out of the vessel 23 by the high pressure air A. Consequently, unlike the compressor 4 of the conventional apparatus shown in FIG. 22, the blower 31 is not subjected to a hot and corrosive steam so that its longevity is not shortened by the steam. In short, appropriate durability is insured. Further, the deodorant unit 22 which includes the air cooled type condenser 32 is provided downstream of the exit of the vessel 23, the installation of the apparatus becomes easier. The running cost of the apparatus becomes also less expensive since no water charges are needed as compared with a water cooled steam separator. The gas G generated upon gas/liquid separation in the condenser 32 is heated for deodorization and the deodorant heater 33 is a compact one so that space saving and environmental conservation are achieved. Since the heat exchanger 34 is provided at the end of the air discharge pipe 81 and the start of the air inlet pipe 30, the entering air A is heated before it is supplied into the heating vessel 23 and the outgoing gas G is cooled before it is discharged to the air. The lower the temperature, the less smelly the expelled gas. Since the blower 31 is provided upstream of the heat exchanger 34, it is not damaged by the air A having an elevated temperature raised upon heat exchange by the heat exchanger 34.

In this embodiment, the motor 28 is situated next to a lateral wall of the heating vessel unit 25 and is coupled to the rotary pulverizer/stirrer 26 by the power transmission mechanism 29, but the motor 28 may be located immediately below the lower end of the shaft 54 of the rotary pulverizer/stirrer 26 and coupled thereto directly to dispense with the power transmission mechanism 29. Furthermore, the deodorant heater 33 and the heat exchanger 34 are illustrated to be vertical type ones respectively, but they may be horizontal ones. In addition, the condenser 32 may be cooled by a high pressure air. If the circumstances demand, the condenser 32 may be water cooled.

Figure 1:
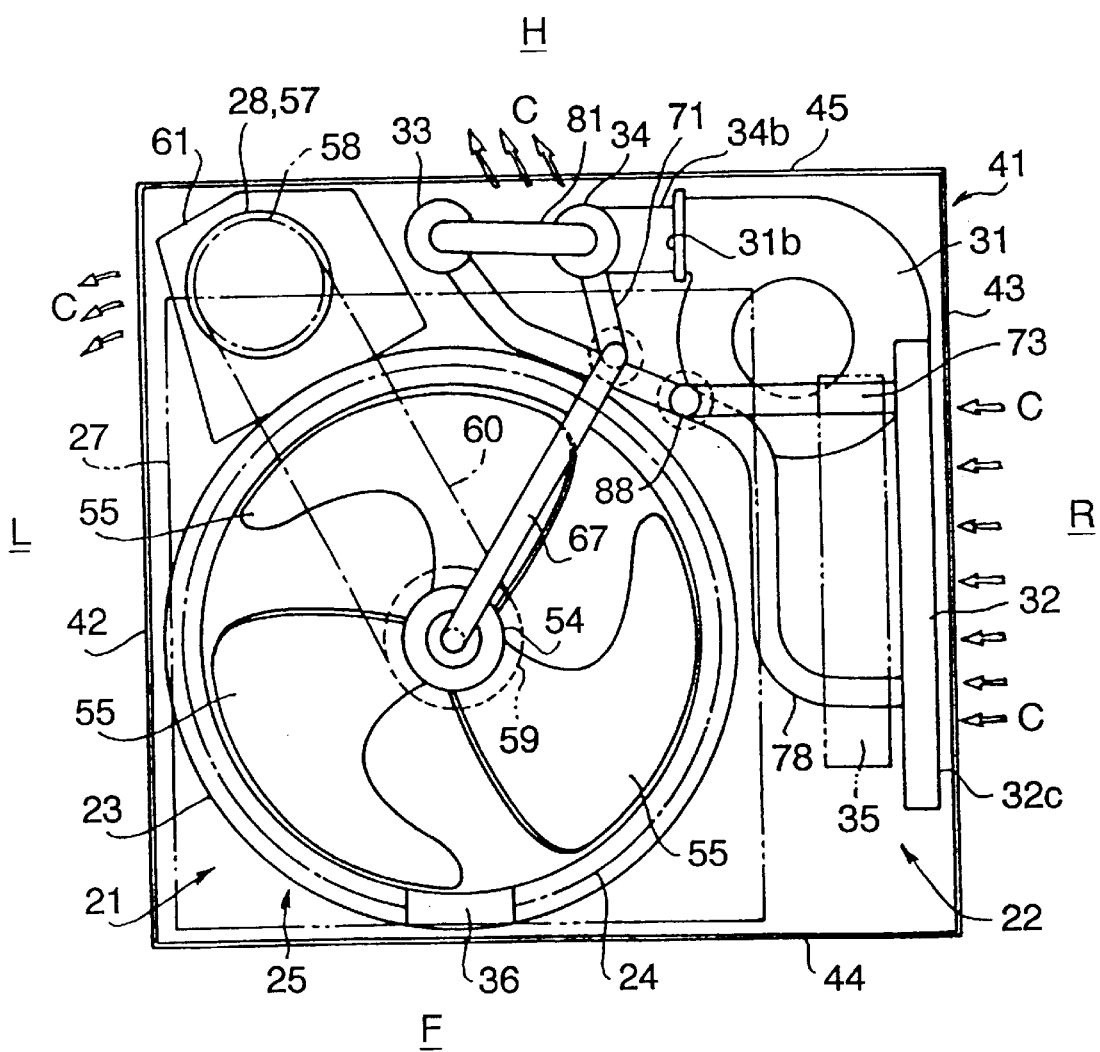
FIG. 1 shows a plan cross section of a garbage processing apparatus according to a first embodiment of the present invention.
Figure 2:
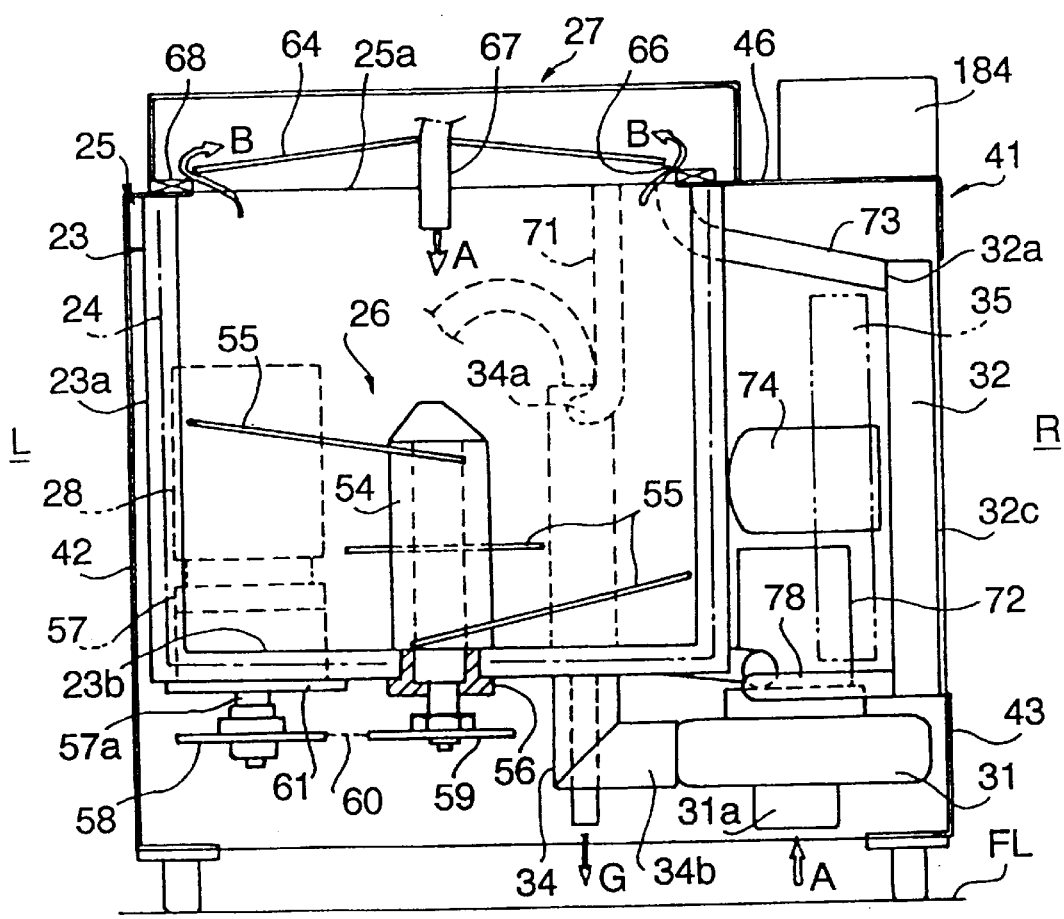
FIG. 2 is a front cross section of the apparatus shown in FIG. 1.
Figure 3:
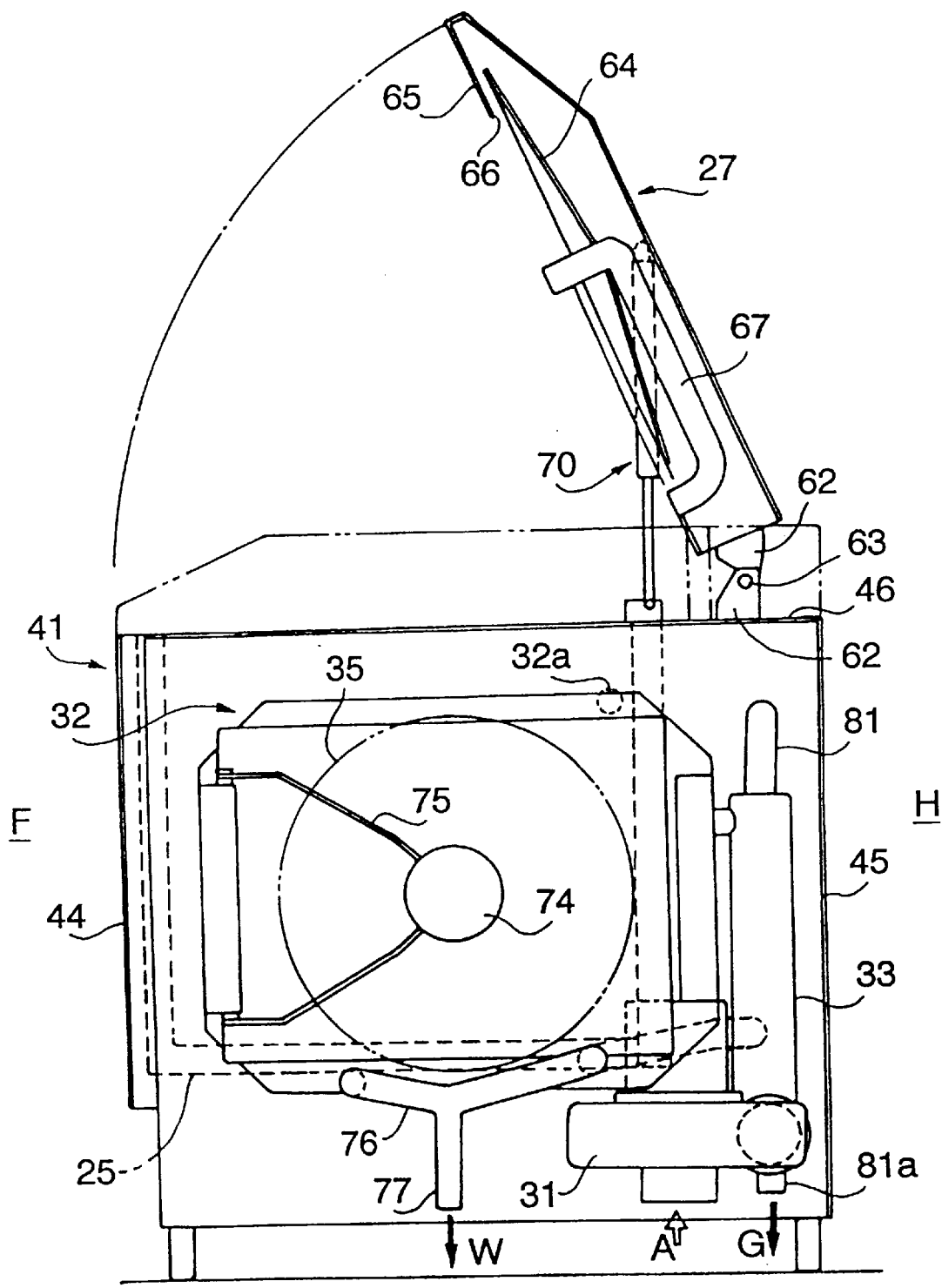
FIG. 3 is a lateral cross section of the apparatus shown in FIG. 1.

Referring now to FIGS. 1 to 3, the detailed structures of the heating mechanism 21 and deodorization mechanism 22 will be described. The heating vessel unit 25 of the heating mechanism 21 includes the heat resisting vessel 23 which is designed to be able to process about 50 kg of garbage, for example, and the heater 24 buried in a peripheral wall 23a and a bottom wall 23b of the vessel 23. The vessel 23 has a cylindrical body and a bottom. Its top is open to define a garbage inlet opening 25a. By controllably energizing the heater 24, the interior of the heating vessel 23 is maintained to a prescribed temperature such as 100 to 125° C. which is a suitable temperature for drying of the garbage. It should be noted that the outer surface of the heating vessel 23 is covered with a heat insulator (not shown). As mentioned earlier, the solid matter of the garbage generated upon the drying operation in the heating vessel 23 is discharged from the outlet 36 of the vessel 23. This outlet 36 is formed in a front lower portion of the peripheral wall 23a of the vessel 23. "F" designates the front side of the vessel 23. The heating vessel unit 25 is supported in a box-like housing 41.

Figure 10:
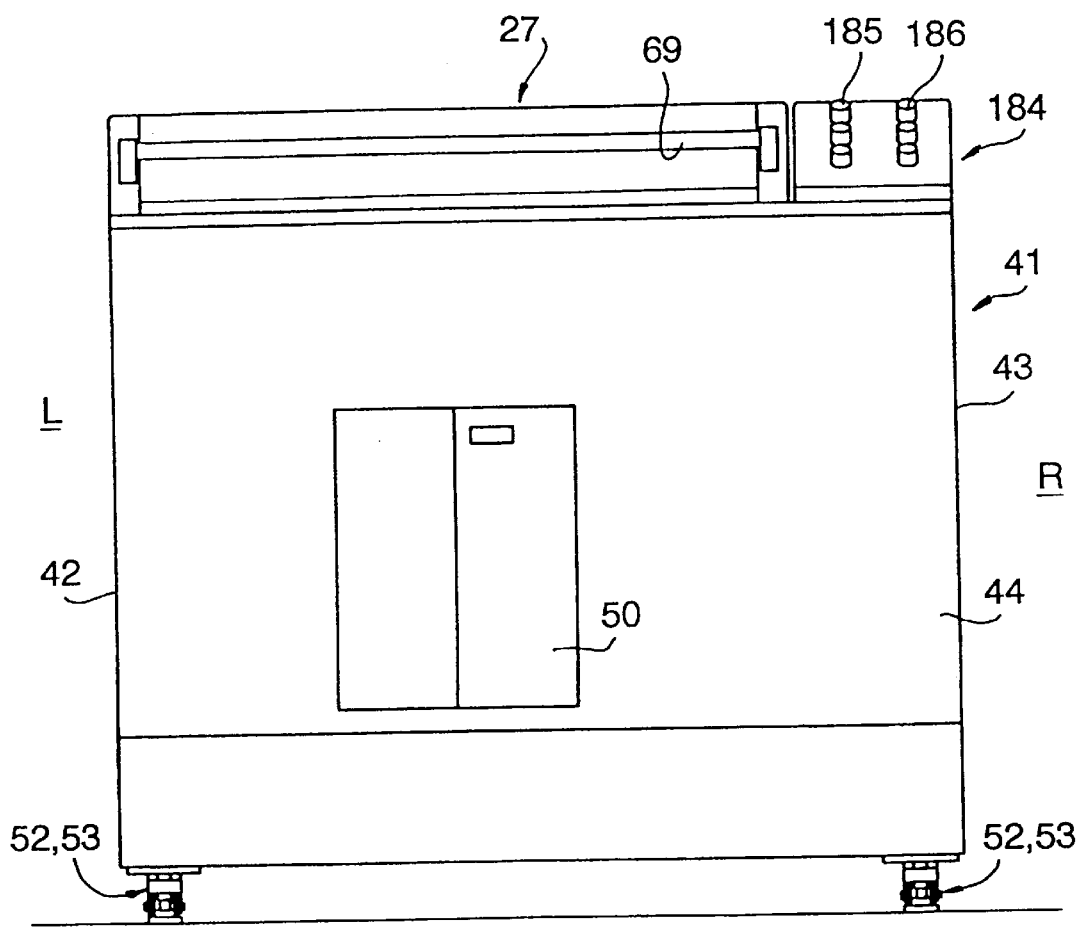
FIG. 10 is a front view of the garbage processing apparatus which corresponds to FIG. 2.
Figure 11:
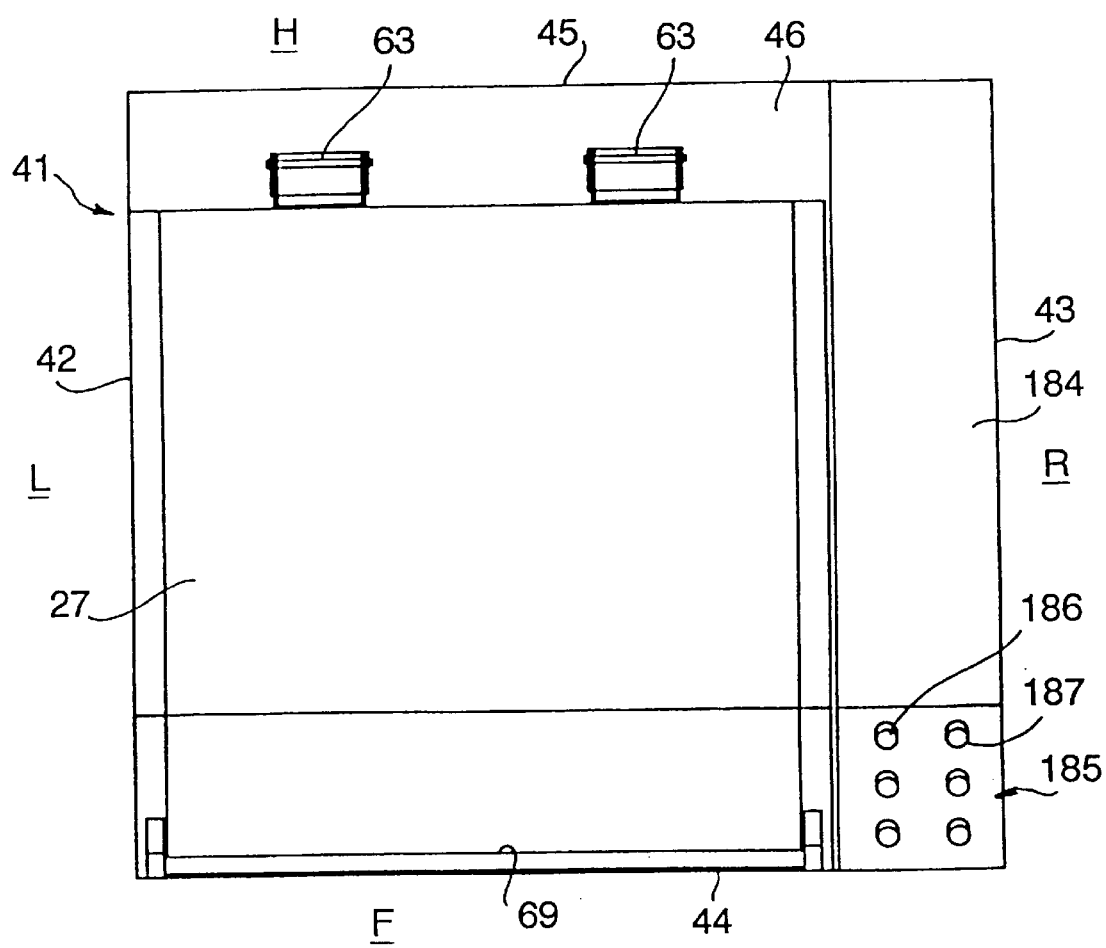
FIG. 11 is a plan view of the garbage processing apparatus which corresponds to FIG. 1.
Figure 12:
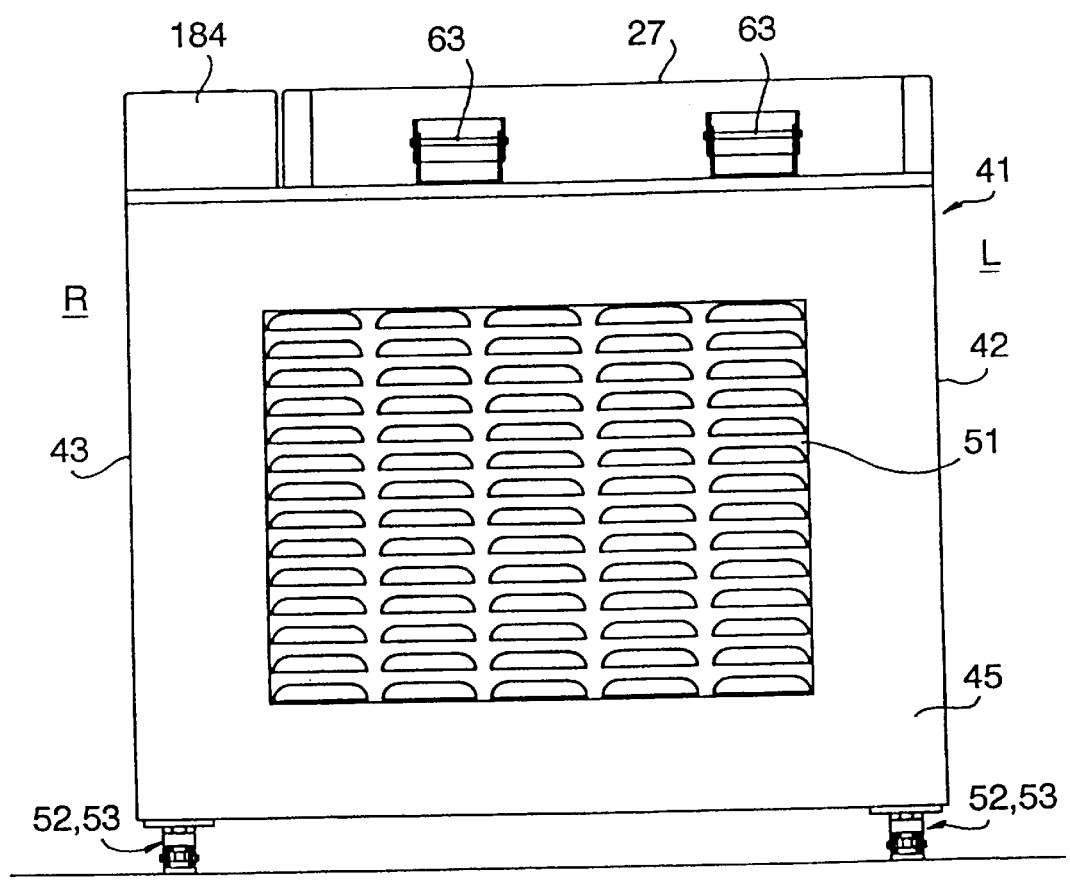
FIG. 12 is a rear view of the garbage processing apparatus.
Figure 13:
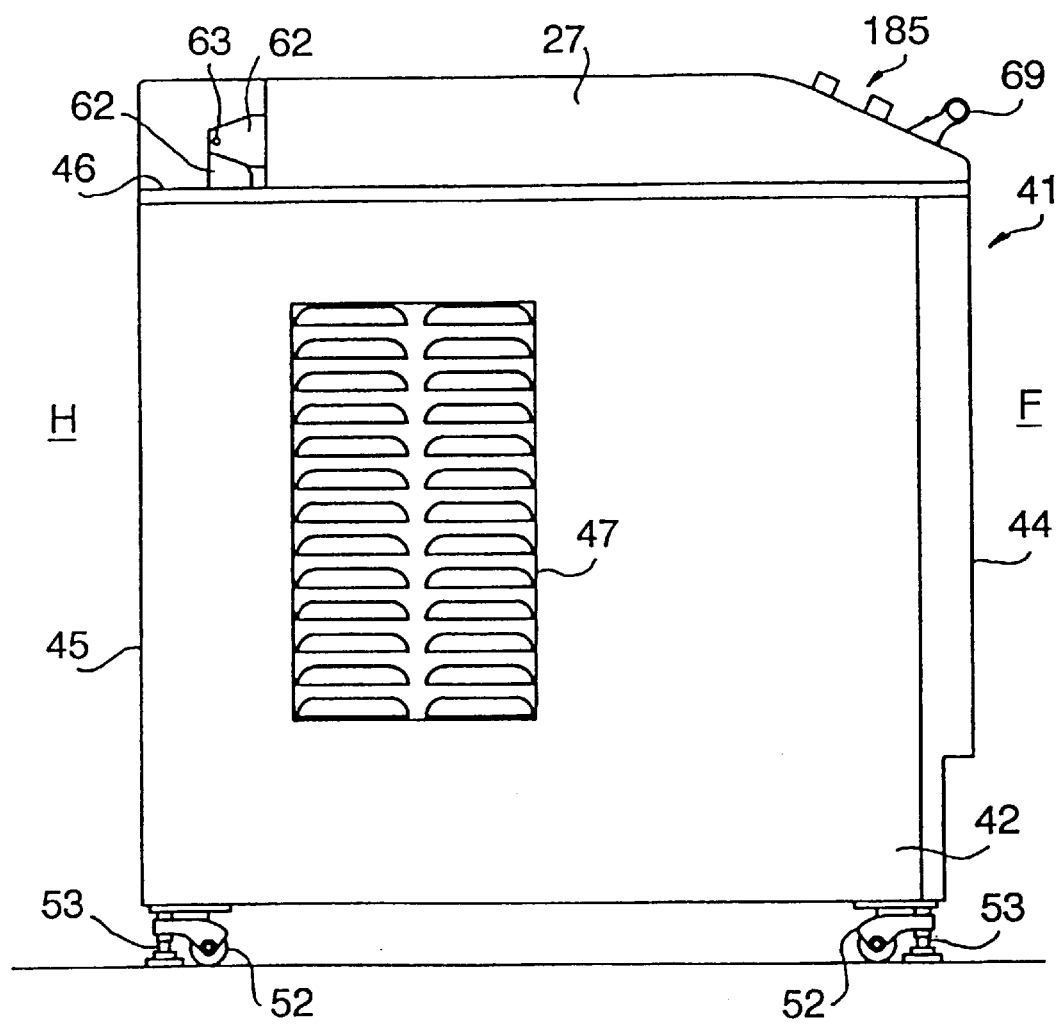
FIG. 13 is a left side view of the garbage processing apparatus.
Figure 14:
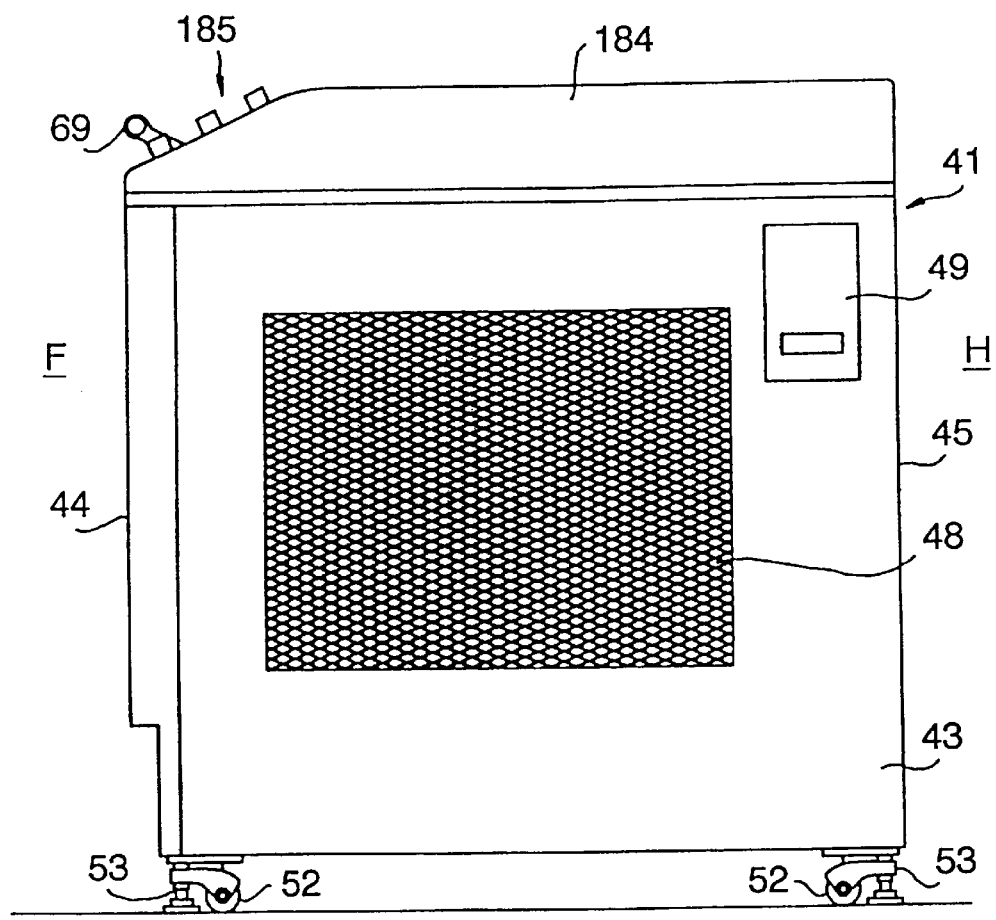
FIG. 14 illustrates a right side view of the garbage processing apparatus which corresponds to FIG. 3.

As also illustrated in FIGS. 10 to 14, the housing 41 has a left side plate 42, a right side plate 43, a front plate 44, a back plate 45 and a roof plate 46. All of these plates may be made from stainless. The illustrated housing 41 has a generally cubical shape defined by these plates. "L" designates the left, "R" designates the right and "H" designates the back. Referring to FIG. 2, the roof plate 46 has an opening which corresponds to the garbage inlet opening 25a of the heating vessel 25 and is secured to an upper edge of the peripheral wall 23a of the vessel 23. As illustrated in FIG. 13, the left side plate 42 has a ventilation panel 47 which has a number of slits. As illustrated in FIG. 14, the right side plate 43 also has a ventilation panel 48 made from a net or the like and a small openable window plate 49 for observation of the inside of the heating vessel 25. As illustrated in FIG. 10, the front plate 44 has a pair of biparting doors 50 at a position corresponding to the solid garbage outlet opening 36 of the heating vessel 25. As illustrated in FIG. 12, the back plate 45 has a relatively large ventilation panel 51 having a number of slits like the one shown in FIG. 13. Inside the housing 41, provided are support frame members (not shown) for supporting the heating vessel 25. The frame members may extend in Longitudinally, transversally and/or diagonally in horizontal and/or vertical direction. The heating vessel 25 is located in the housing 41 as depicted in FIG. 1. Specifically, the heating vessel 25 is close to the front and left plates 44 and 42 and has some clearance from the back and right plates 45 and 43. In other words, a space for reception of parts of the deodorization mechanism 22 is formed in the housing 41 on the back and right sides H and R. As understood from FIGS. 12 to 14, the housing 41 has pedestal members 54 and associated casters 54 at four corners of its bottom plate.

Referring to FIG. 2, the stirring device 26 includes the rotary shaft 54 extending vertically along the center axis of the vessel 23 until the approximate middle of the vessel 23 and three blades 55 radially and slightly upward extending from the rotary shaft 54 until the vicinity of the peripheral wall 23a of the vessel 23. The three blades 55 are spaced in the vertical direction as well as in the circumferential direction at constant intervals. Arrangement, shape and material of the blades 55 are determined such that the blades 55 can appropriately pulverize and stir the garbage as fed from the garbage inlet of the vessel 23 when they rotate in the vessel 23. The shaft 54 is supported from the bottom wall 23b of the vessel 23 via a bearing 56. The height of the shaft 54 is about a half of that of the vessel 23. The lower end of the shaft 54 terminates below the lower wall 23a of the vessel 23 and has a sprocket 59 mounted thereon. As illustrated in FIG. 1, the motor 28 is vertically placed next to the heating vessel 23 in the housing 41 at the rear left corner of the housing. As shown in FIG. 2, an output shaft of the motor 28 extends from the bottom of the motor 28 and is coupled to a speed reduction mechanism 57, and an output shaft 57a of the speed reduction mechanism 57 penetrates the bottom wall 23a of the vessel 23 and has a sprocket 58 at its end. The sprocket 58 is coupled to the sprocket 59 of the rotating shaft 54 by a chain 60. Accordingly, the sprockets 58 and 59, the chain 60 and the speed reduction unit 57 in combination form the power transmission mechanism to transmit the drive power of the motor 28 to the rotary pulverizer/stirrer 26. The motor 28 and the speed reduction unit 57 are secured in the housing 41 by a bracket plate 61 and supporting frame (not shown).

The lid 27 of the heating vessel unit 25 has a generally square shape as viewed from the top, and is pivotably connected to the top plate 46 of the housing 41 along its rear edge by brackets 62 and a pin 63 as depicted in FIG. 13. Referring to FIG. 3, the inner face of the lid 27 is defined by the shallow conical inner member 64 having a size in conformity with the heating vessel 23. The outer periphery of the lid 27 is bent inward to form an inwardly directed flange portion 65 which spacedly underlies part of the inner lid 64 of the lid 27. A gap between the outer lid 27 and the inner lid 64 defines an annular steam outlet opening 66 through which the steam B flows to the pipe 73 from the heating vessel unit 25 (FIG. 2). The most downstream segment of the air inlet passage 30 is designated at 67. The downstream quarter of this pipe segment 67 penetrates the inner lid 64 perpendicularly downward along the center axis of the inner lid 64. The lid 27 is biased upward by a pair of gas springs 70 spanning the lid 27 and the top plate 46 of the housing 41 (only one spring 70 is illustrated in FIG. 3). When the lid 27 is moved to a closed position, the pipe segment 67 projects in the vessel 23 to a certain extent as illustrated in FIG. 2. A packing 68 is provided on the flange 65 of the outer lid 27 such that the packing 68 extends along the periphery of the garbage inlet opening 25a for air tightness of the heating vessel 25. As shown in FIGS. 13 and 14, the lid 27 has a handle 69 on its front side such that an operator can open the lid 27.

Figure 5:
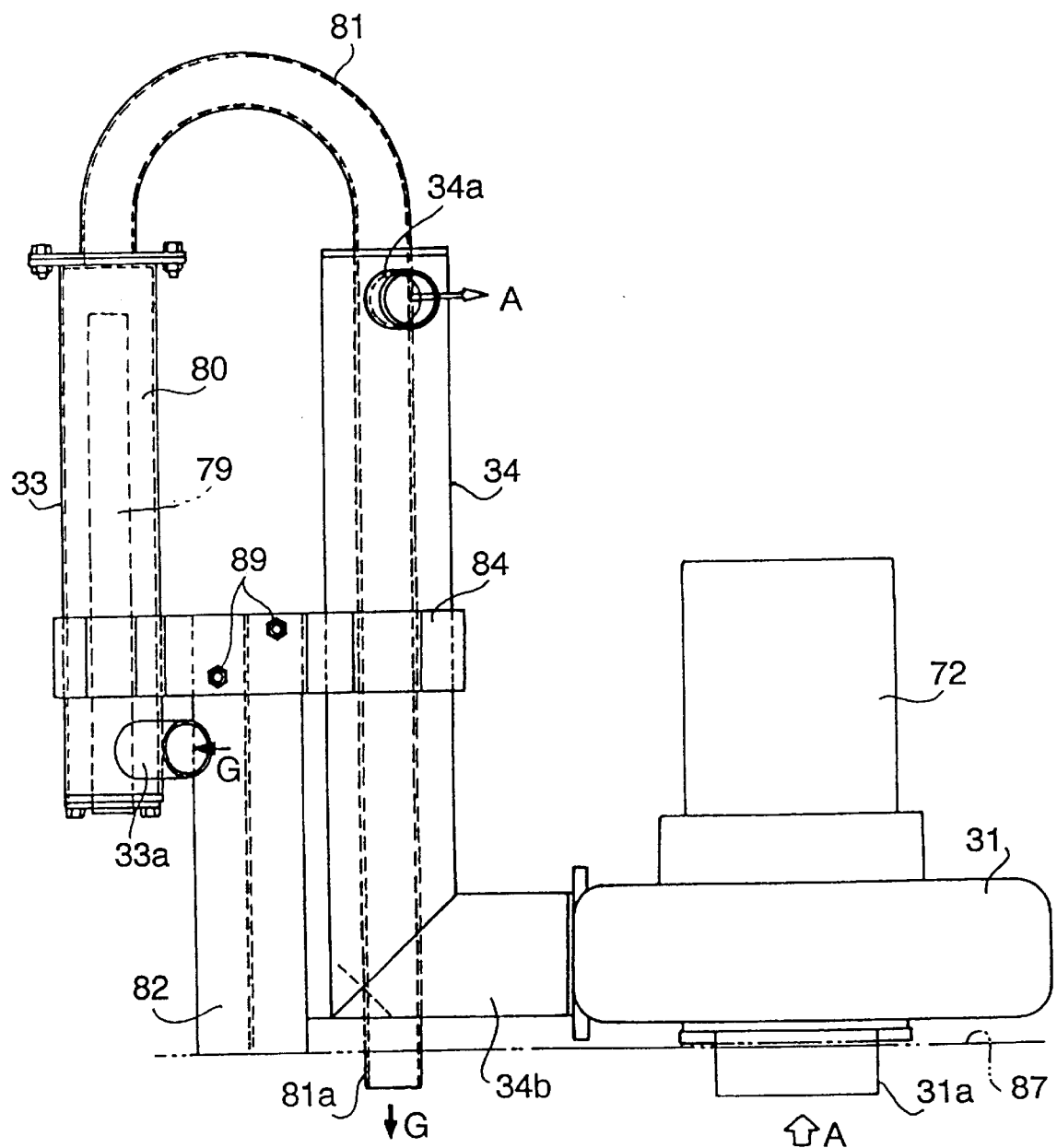
FIG. 5 illustrates a front view of a deodorant heater, heat exchanger and blower of the apparatus shown in FIG. 1 with other parts being omitted for clarification.
Figure 6:
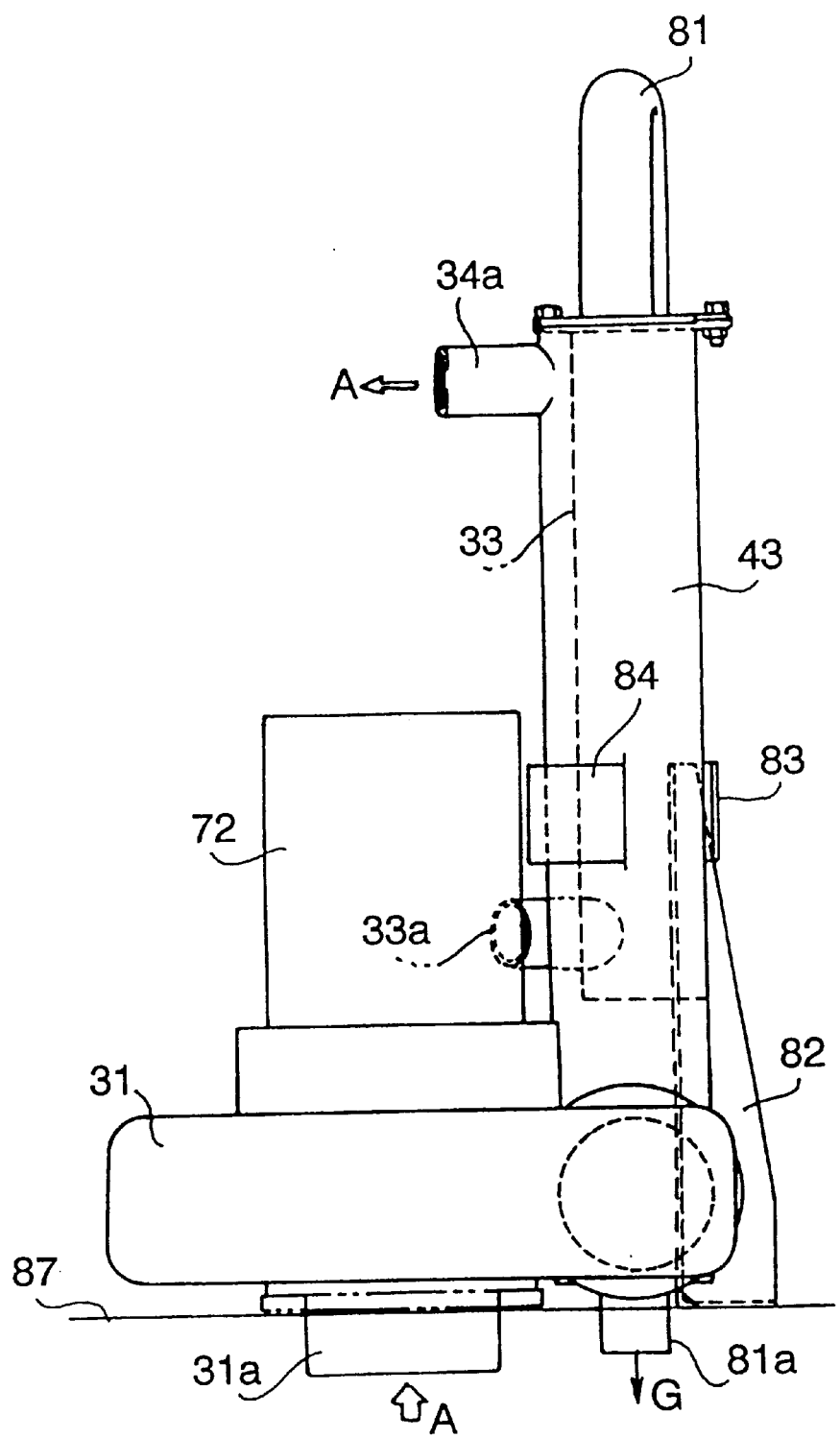
FIG. 6 illustrates a side view of the heater, heat exchanger and blower shown in FIG. 5.

Referring to FIG. 1, the downstream end pipe segment 67 of the air inlet passage 30 extends in an upper right direction from the center of the lid 27 as viewed from the top, and bends downward so that it connects to another pipe segment 71. The pipe segment 67 is detachable from the pipe segment 71. The pipe segment 67 is connected to the pipe segment 71 upon closing the lid 27. As indicated by the imaginary line in FIG. 2, the pipe segment 71 extends vertically downward. The lower end of the pipe segment 71 bends at right angle and extends to an outlet 34a of the heat exchanger 34. The cylindrical heat exchanger 34 stands in the vicinity of the back plate 45. An inlet 34b of the heat exchanger 34 extends at right angle from the vertical main body of the heat exchanger along the back plate 45 (FIG. 1) and reaches an outlet 31b of the blower 31. As best illustrated in FIG. 1, the blower 31 is located at a rear right corner of the housing 41. As depicted in FIG. 2, an inlet 31a of the blower 31 is directed downward to take in the fresh air A from a clearance between the housing 41 and a floor FL. The blower 31 is a centrifugal blower having an impeller therein (not shown) and supported on a frame 87 (FIG. 5) such that an axis of rotation of the impeller extends vertically and the outlet 31b of the blower 31 is directed horizontally along the rear plate 45 of the housing (FIG. 1). As depicted in FIG. 5, an electric motor 72 is placed on the blower 31 such that a shaft (not shown) of the impeller (not shown) of the blower 31 is driven by the motor 72.

The condenser 32 of the deodorant mechanism 22 includes a plate-type (i.e., thin rectangular parallelopiped) casing 32c, a tube (not shown) extending in the casing 32c and fins (not shown). As best illustrated in FIGS. 1 and 2, the condenser 32 stands along the right wall 43 of the housing 41. The condenser 32 has a steam inlet opening 32a near its upper rear corner. The pipe 73 extends to this steam inlet opening 32a from an opening 88 (FIG. 1) formed in the inner flange 65 of the lid 27 of the garbage heating vessel 23 when the lid 27 is in the closed position. Next to the condenser 32 in the housing 41, provided is the axial cooling fan 35. An axis of rotation of the cooling fan 35 is directed in a direction perpendicular to the plate type casing 32c of the condenser 32. A drive motor 74 (FIG. 2) for actuating the cooling fan 35 is directly coupled to a rotating shaft (not shown) of the cooling fan 35. The fan motor 74 is supported by linkages 75 as shown in FIG. 3. Upon rotation of the cooling fan 35, an external air is introduced into the housing toward the condenser 32 from the right wall 43 of the housing 41 as indicated by the left directed unshaded arrows C in FIG. 1. Specifically, as illustrated in FIG. 14, the external air C flows into the housing 41 from the mesh panel 48. Accordingly, the condenser 32 is air cooled. After passing through the condenser 32, the air C is directed to the rear wall 45 and left wall 42 of the housing 41 as it passes by the lateral portion of the vessel unit 25. Specifically, the air C flows out of the housing 41 from the panel 51 of the rear plate 45 (FIG. 12) and the panel 47 of the left plate 42 (FIG. 13) of the housing 41. Thus, the air C which gains the heat as it flows through the condenser 32 is not confined in the housing 41 and temperature elevation of the parts in the housing 41 such as the motor 28 is prevented. The separated gas G is introduced by the pipe 78 to the deodorant heater 33 located between the motor 28 and the heat exchanger 34. The pipe 78 extends to a lower gas inlet opening 33a (FIG. 5) of the deodorant heater 33 from the lower front corner of the condenser 32 generally along the heating vessel 23 in a direction toward the rear plate 45 of the housing diagonally. As illustrated in FIG. 3, a plurality of drain pipes 76 extends downward from a lower portion of the condenser 32 and joins to a single discharge pipe 77 such that the condensed water W is discharged to the outside from the condenser 32 by the discharge pipe 77.

Figure 7:
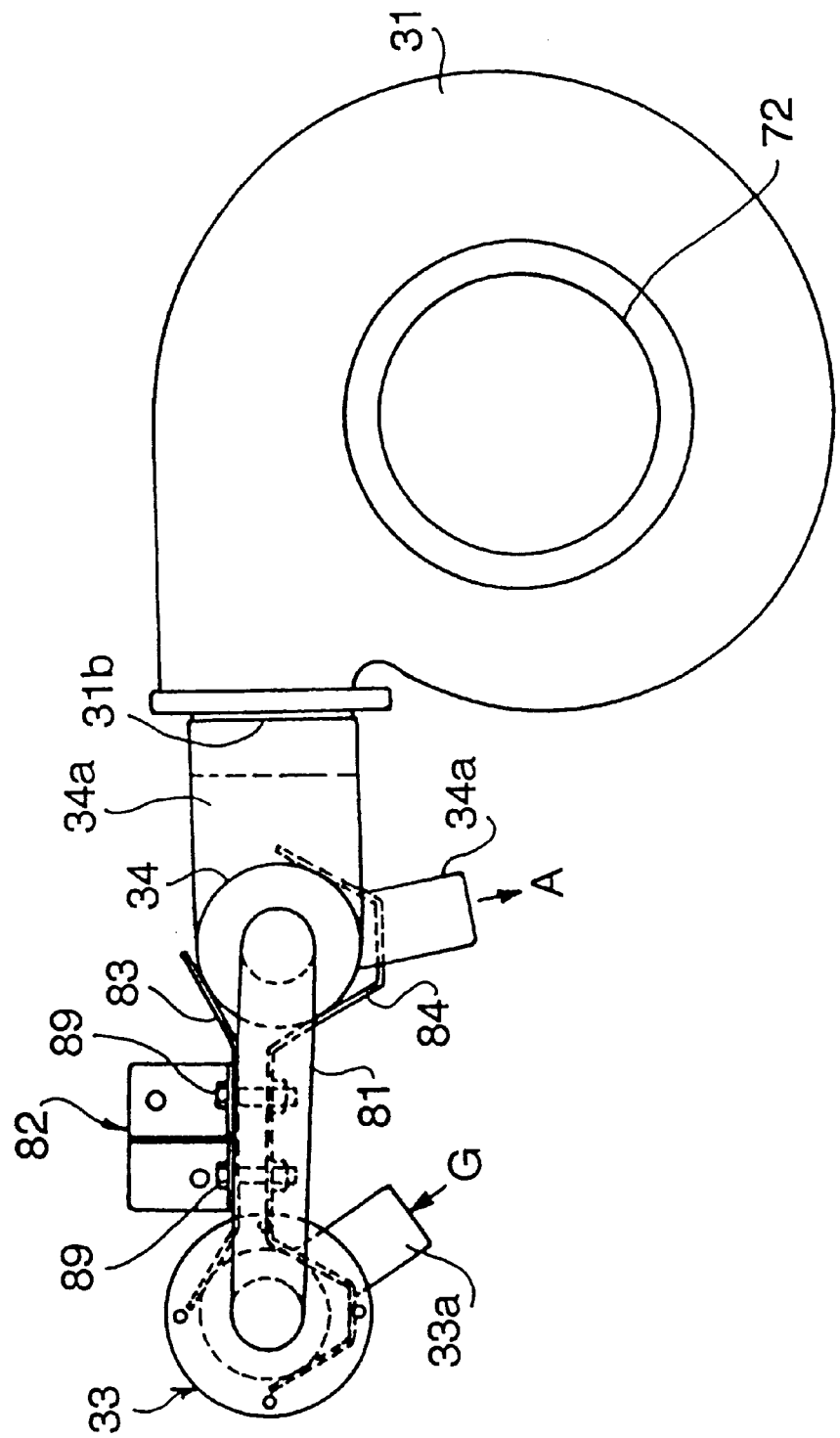
FIG. 7 illustrates a top view of the heater, heat exchanger and blower shown in FIG. 5.

Referring to FIG. 5, the deodorant heater unit 33 has a vertically elongated cylindrical casing, the coaxially extending heater element 79 in the casing and a thermal medium 80 such as a ceramic particle filled around the heater element 79 in the casing. Upon heat generation by the heater 79, the gas G is heated to a predetermined high temperature, for example 500 to 600° C., as the gas flows through the thermal medium 80. The gas G is accordingly oxidized so that its odor is removed. The gas G enters the deodorant heater 33 from the lower gas inlet 33a and flows upward toward an upper exit. The inverted J-shaped pipe 81 extends from the gas exit of the deodorant heater 33 and penetrates the heat exchanger 34 coaxially such that the gas G is discharged to the atmosphere from its exit 81a after it is heat exchanged with the relatively cold fresh air A fed from the blower 31. This heat exchange is best depicted in FIG. 4. The deodorant heater 33 and heat exchanger 34 are supported in a parallel upstanding relationship by a pair of horizontal bracket plates 83 and 84 and a vertical support plate 82 for mounting the bracket plates 83 and 84 horizontally at its top as shown in FIGS. 5 to 8. The support plate 82 extends vertically upward from the frame 87 in the housing 41. As best seen in FIG. 7, the bracket plates 83 and 84 are joined with the support plate 82 at their center portions respectively by bolts 89 and bent outward at ends to hold or clamp the deodorant heater 33 and heat exchanger 34 in position respectively.

Figure 8:
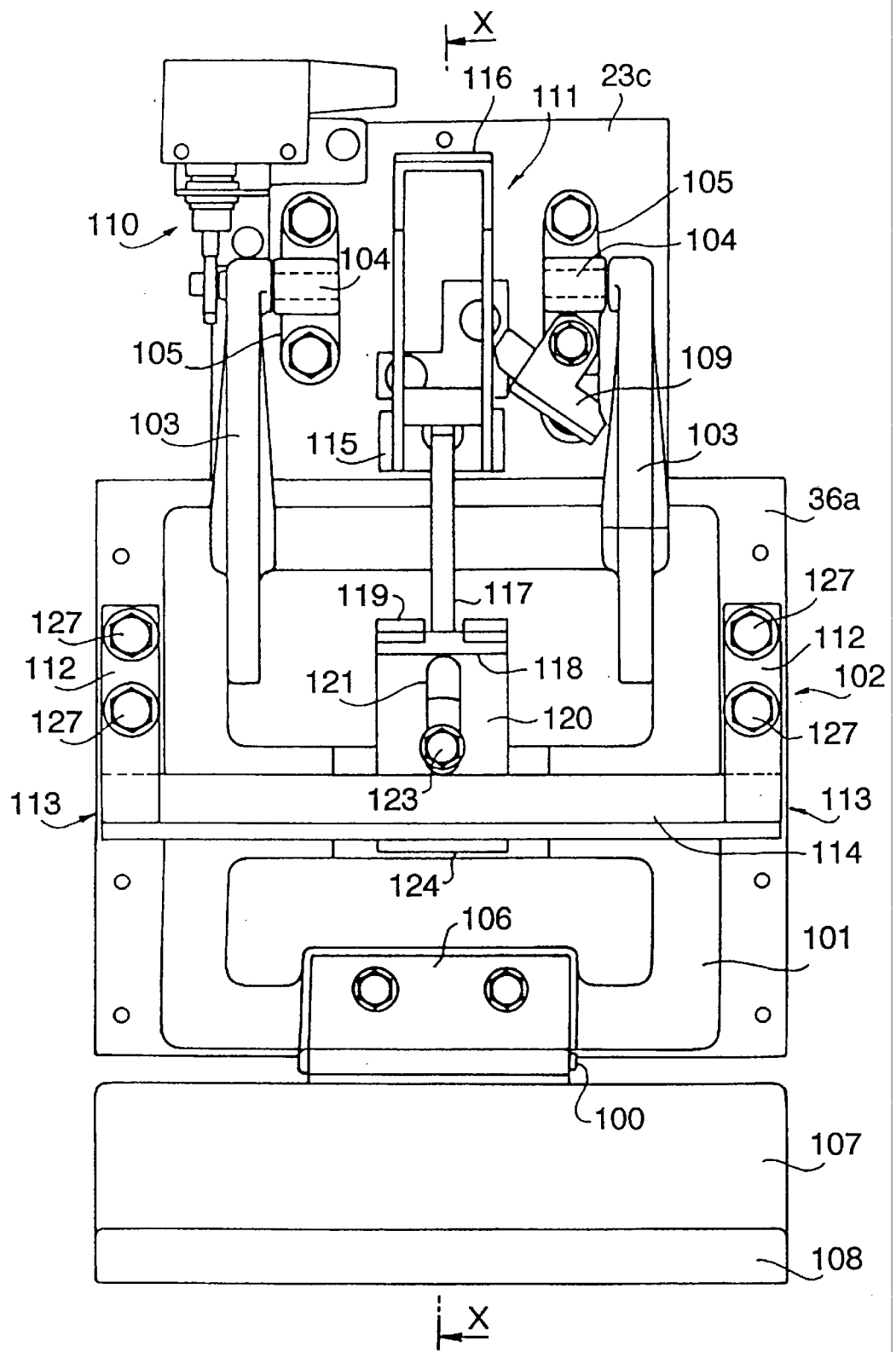
FIG. 8 depicts a door structure for closing and opening a dried garbage discharge opening.
Figure 9:
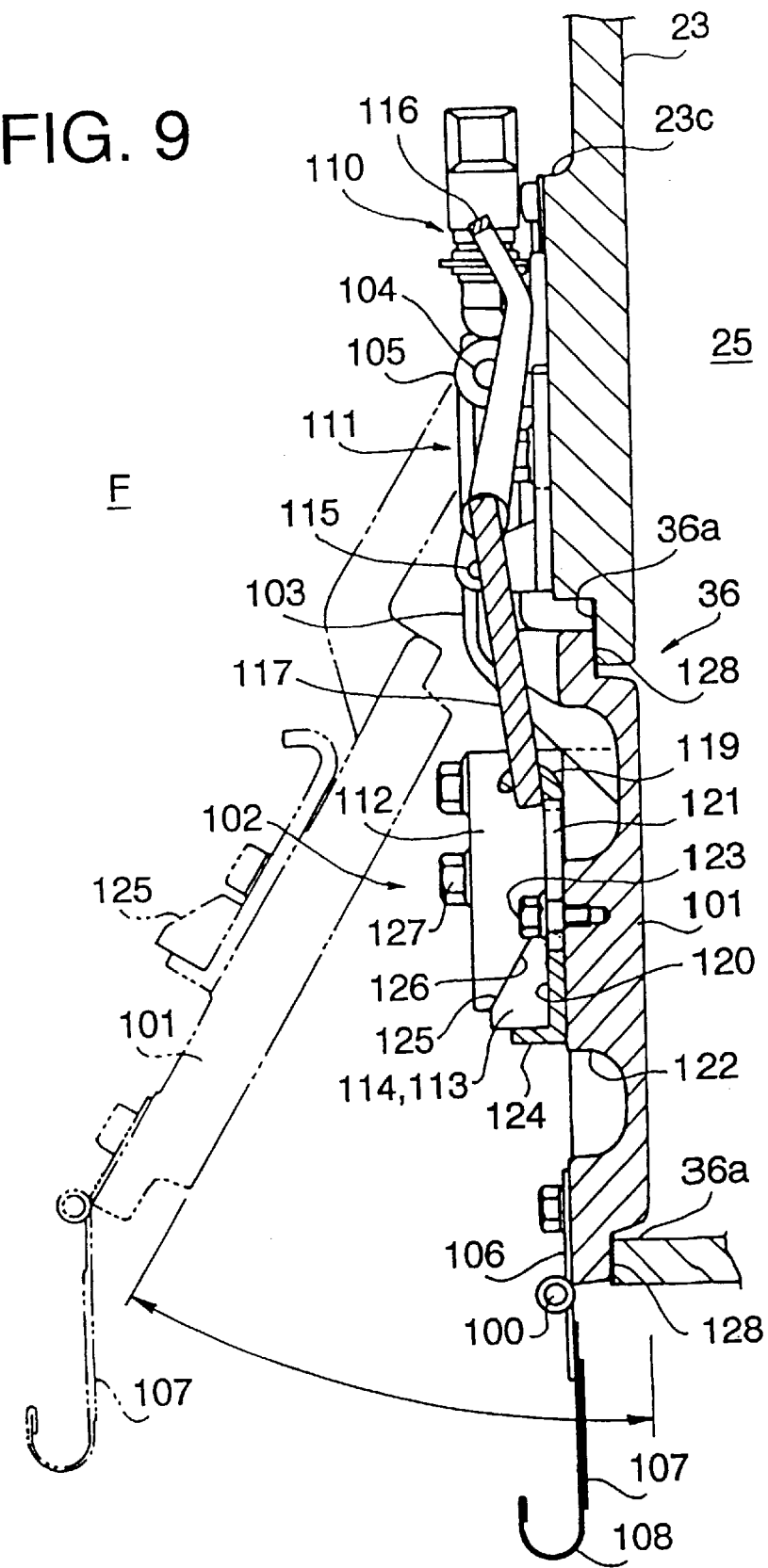
FIG. 9 is a cross section taken along the line X—X of FIG. 8.

In this embodiment, the dried garbage is discharged to the outside from the lower front outlet opening 36 of the heating vessel 25. The outlet opening 36 is closed and opened by a door 101 and a door locking mechanism 102 as illustrated in FIGS. 8 and 9.

The door 101 is a thick plate member and has a generally square shape which corresponds to the shape of the outlet opening 36. The door 101 has substantially the same thermal resistance as the heating vessel 23. The periphery of the door 101 is reduced in thickness to form a stepwise portion which seats on a mating stepwise portion formed in the periphery 36a of the garbage outlet 36 as best shown in FIG. 9. A packing 128 is provided along the stepwise portion of the periphery 36a. A pair of parallel arms 103 extends upward from a front upper surface of the door 101 to a pair of horizontal shafts 104. The shafts 104 are rotatably supported on a relatively thick portion 23c of the heating vessel 23 by brackets 105 respectively. Thus, the door 101 is pivotable forward about the transversal shafts 104 to open the dried garbage outlet 36 upon clockwise movement of the arms 103 in FIG. 9 as indicated by the imaginary line. A rectangular plate 107 which has the same width as the door 101 hangs from a lower edge of the door 101 using a bracket plate 106 and a transversal pin 100, and has a handle 108 along its lower edge. The handle 108 has a U-shaped cross section. While the door 101 is moving to the open position, the plate 107 maintains the vertical posture so that scattering of the garbage pushed out of the vessel 23 is prevented by the plate 107. A stopper 109 is provided on the thicker portion 23c of the drying vessel 23 in the vicinity of one of the brackets 105 to fix the door 101 in the open position. In the open position, the door 101 may be held in an about 30-degree inclined posture as shown in FIG. 9. The stopper 109 pivots counterclockwise in FIG. 8 by its weight and engages with the associated arm 103 when the door 101 is opened. Near the shaft 104 of the other arm 103, provided is a sensor (e.g., proximity switch) 110 for detection of the opening and closing of the door 101.

The locking means 102 is provided for locking the door 101 in the closed position. The locking means 102 includes a fastener 111 for a manual locking operation, two pairs of mating wedge blocks 112 and 113 for converting an upper sliding movement of the blocks 113 into a door pushing (or locking) movement toward the rear H and a bar 114 for transferring a manually operating power of an operator from the fastener 111 to the blocks 112 and 113. The fastener 111 includes a handle 116 having an inverted U shape as viewed from the front and pivotably attached to the thicker wall 23c of the heating vessel 23 at ends by a transverse pin 115, an arm 117 extending downward from the handle 116, another transverse shaft 118 attached to a lower end of the arm 117 and a slide plate 120 having a curved portion 119 engaged with the transverse shaft 118. The slide plate 120 also has a vertically elongated hole 121 which loosely engages with a bolt 123 projecting forward from a center portion 122 of the door 101. Accordingly, when the handle 116 is pivoted about the transverse pin 115 downward or counterclockwise in FIG. 9, the slide plate 120 is shifted or slid downward on the center portion 122 as the arm 117 moves downward. The slide movement of the plate 120 is restricted and guided by the elongated hole 121 and the fitting bolt 123. The slide plate 120 has a flange 124 along its lower edge for holding the transverse bar 114. The wedge blocks 113 are formed at ends of the transverse bar 114. As best illustrated in FIG. 9, each of the wedge blocks 113 has a generally right angled triangle cross section with its oblique line being directed forward and upward to define a wedge surface 125. In this particular embodiment, the bar 114 has the same cross section as the wedge blocks 113. The blocks 113 therefore move together with the slide plate 120. The mating blocks 112 are stationary blocks. Each of the blocks 112 has a wedge surface 126 in slidable contact with the wedge surface 125 of the associated block 113. The wedge surface 126 is directed rearward and downward. The wedge blocks 112 a re secured on the periphery 36a of the garbage outlet 36 by bolts 127 (FIG. 8). Consequently, when the blocks 1 13 are moved upward upon manipulation of the fastener 111, the bar 114 is forced rearward (to the right in FIG. 9) by the wedging engagement between the blocks 112 and 113, so that the door 101 is pushed against the periphery 36a of the opening 36.

Referring to FIGS. 10 to 14, a control unit 184 is provided on an upper right position of the housing 41 for setting the temperatures of the heaters 34 and 33 respectively. The control unit 184 includes an operation panel 185 on its front side. The operation panel 185 includes a set of buttons 186 for activation/deactivation of the parts of the apparatus 12 and for other purposes and a set of lamps 187 for indication of operation conditions and the like.

In order to start processing of th e garbage using the garbage processing apparatus 12, the lid 27 is first opened by the operator using the handle 69 and the garbage is thrown into the heating vessel 25. Some water is preferably squeezed out from the garbage before it is thrown into the vessel 25. Then, the lid 27 is closed and a certain button among the operation buttons 186 is depressed to activate the drying heater 24 and motor 28 so that the garbage is dried by the heat from the heater 24 while it is crushed and stirred by the stirring device 26. Simultaneously, the blower 31, cooling fan 35 and deodorant heater 33 of the deodorant device 22 are turned on. Therefore, the high pressure fresh air A is supplied into the heating vessel 25 by the blower 31 so that the steam B generated upon the drying operation in the heating vessel 25 is forced out of the heating vessel 25. The steam B flows into the condenser 32 through the pipe 73 and is separated into the condensed water W and the gas G in the condenser 32. The water W is drained out of the condenser 32 from the discharge tube 77. On the other hand, the gas G is guided by the pipe 78 to the deodorant heater 33 located close to the rear plate 45 of the housing 41 and heated in the heater 33 until the gas G is oxidized and deodorized. The. hot gas G is then heat exchanged with the fresh air A in the heat exchanger 34 before it is expelled to the outside.

The garbage drying operation is performed for a predetermined period, e.g., six hours, such that the garbage loses the moisture and its volume and weight is reduced to about one tenth respectively. The resulting solid matter (i.e., dried garbage) is discharged from the outlet 36 of the heating vessel 25 after the heating and stirring/crushing in the vessel 25 is stopped by manipulation of certain buttons on the control panel 184. In order to take out the dried garbage, the doors 51 of the housing 41 are opened and the handle 116 of the fastener 111 is pushed down to unlock the door 101. Then, the plate 107 is pulled forward to cause the door 101 to pivot upward until the stopper 109 automatically moves in a lock position. After the dried garbage is taken out from the heating vessel 25, the stopper 109 is released from the lock position and the door 101 is moved to overlap or close the garbage opening 36. Then, the handle 116 of the fastener 111 is pushed upward to raise the bar 114 so that the slidable blocks 113 are squeezed under the associated stationary blocks 112. As a result, the bar 114 is imposed rearward and the door 101 is firmly secured in position. Therefore, the heating vessel 23 is again in the closed condition and a next drying operation is now ready to start.

Figure 22:
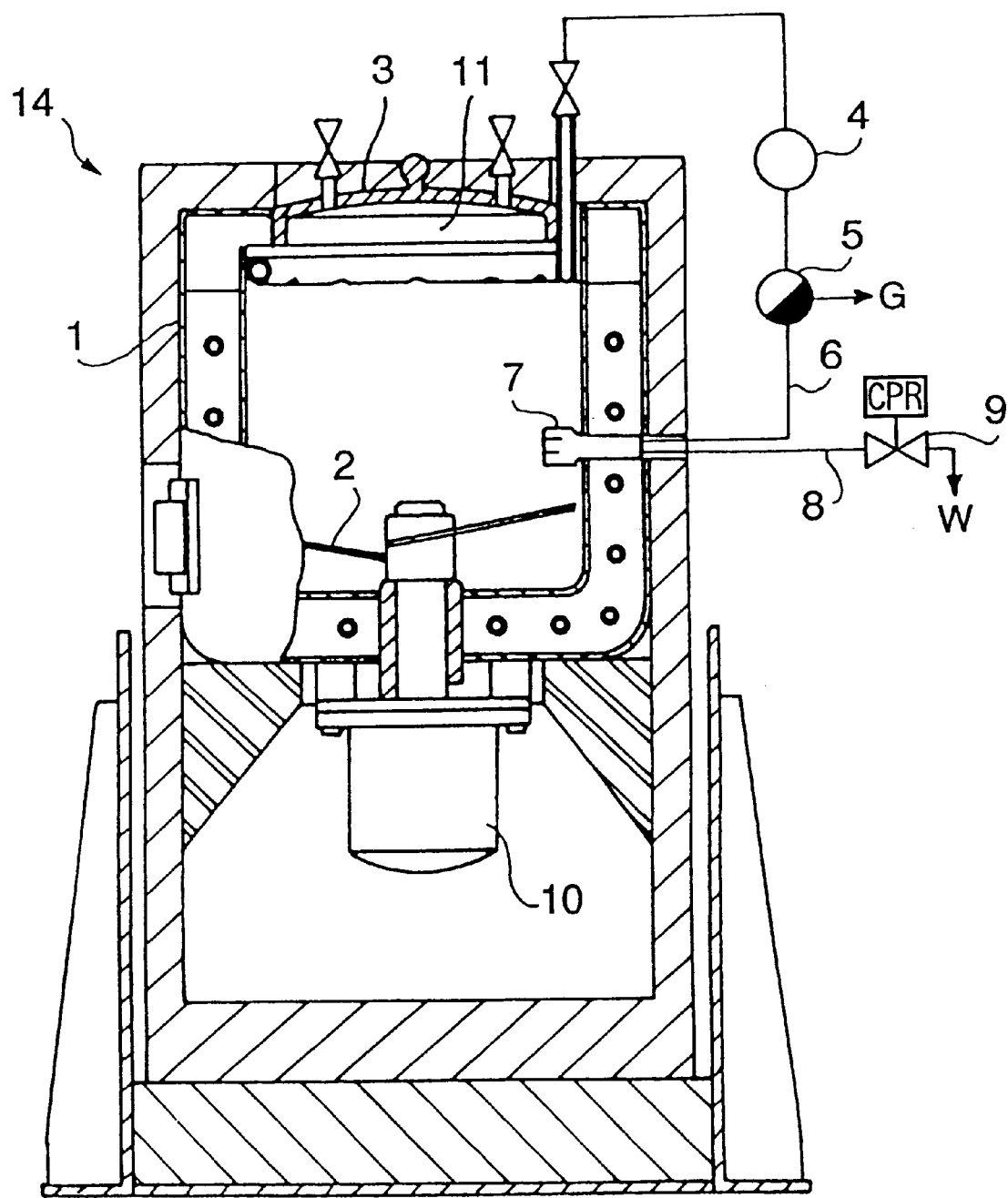
FIG. 22 illustrates a conventional garbage processing apparatus.

Since the motor 28 for driving the stirring member 26 is located next to the heating vessel 25 and the power of the motor 28 is transmitted to the stirring member 26 via the sprockets 58 and 59 and the chain 60, it is possible to design the apparatus 12 in a smaller height as compared with the conventional arrangement shown in FIG. 22. As a result, the garbage inlet opening 25a is lowered so that the garbage feeding operation becomes easier as compared with the conventional arrangement.

Since the vertical condenser 32, the vertical deodorant heater 33 and the vertical heat exchanger 34 are situated next to the heating vessel 25 and these elements are connected by the pipes 67, 71, 73, 77, 78 and 81 appropriately, the apparatus 12 can also be designed in smaller dimensions in width and length directions respectively. This contributes to space saving and raises a degree of freedom in installing the apparatus 12.

Since the condenser 32 is air cooled by the cooling fan 35 and the air C used for the cooling is guided to flow along the heating vessel 25, the temperature elevation in the housing 41 is prevented and thermal damages to the motor 28 is prevented.

Since the fresh air inlet pipe 30 coaxially penetrates the lid 27 so as to feed the fresh air A along the vertical center axis of the heating vessel 25, the incoming air A does not hinder the upward flow of the steam B along the peripheral wall of the heating vessel 25. Therefore, the steam B can be smoothly discharged from the heating vessel 25.

Since the fresh air A is heated as it passes through the heat exchanger 34 and the lid 27, its temperature is already raised to a certain value when it enters the heating vessel 25. Therefore, the energy feeding to the heater coil 24 can be reduced.

Figure 16:
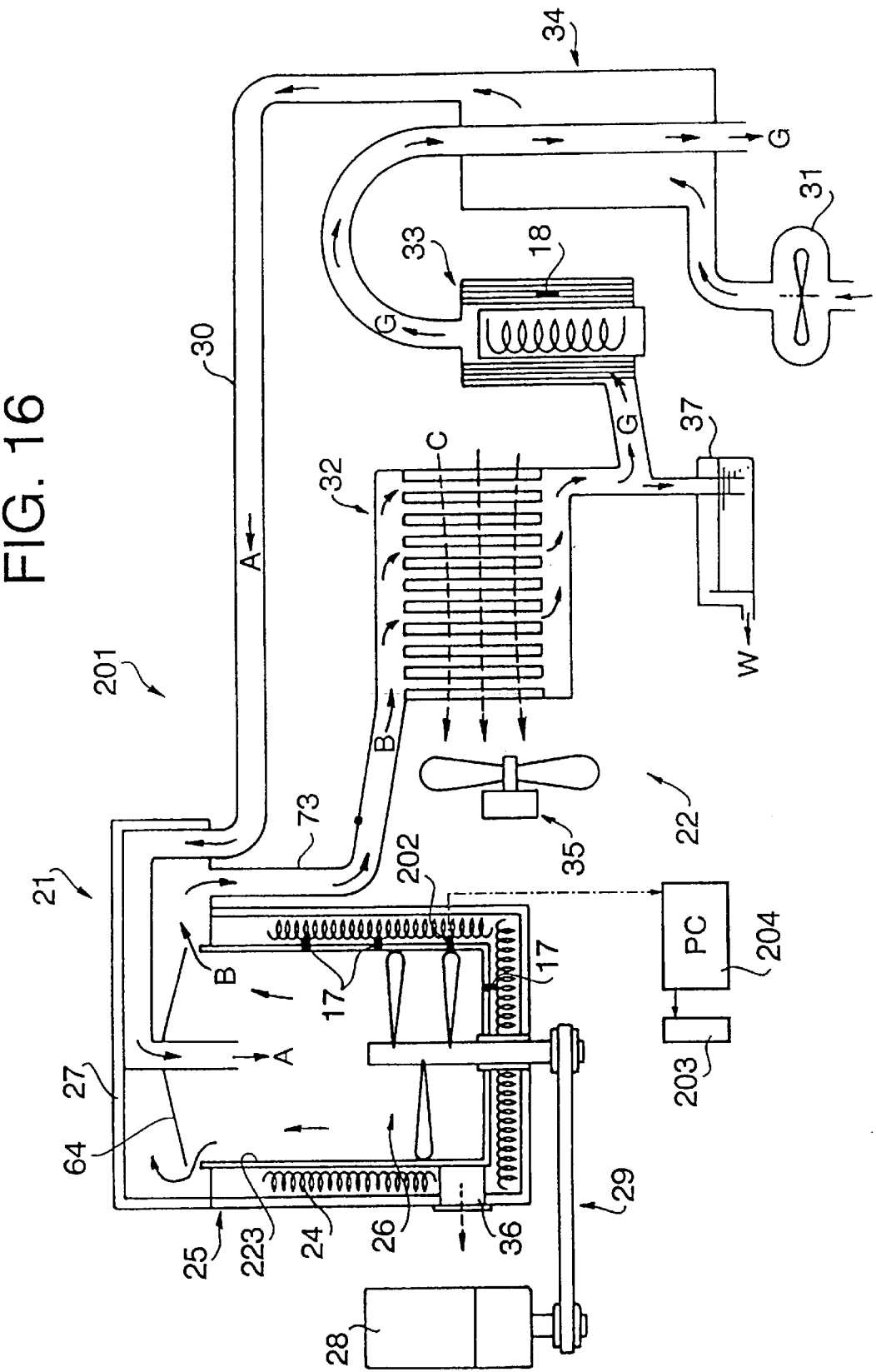
FIG. 16 diagrammatically illustrates an exploded view of a garbage processing apparatus according to a second embodiment of the present invention.
Figure 16A:
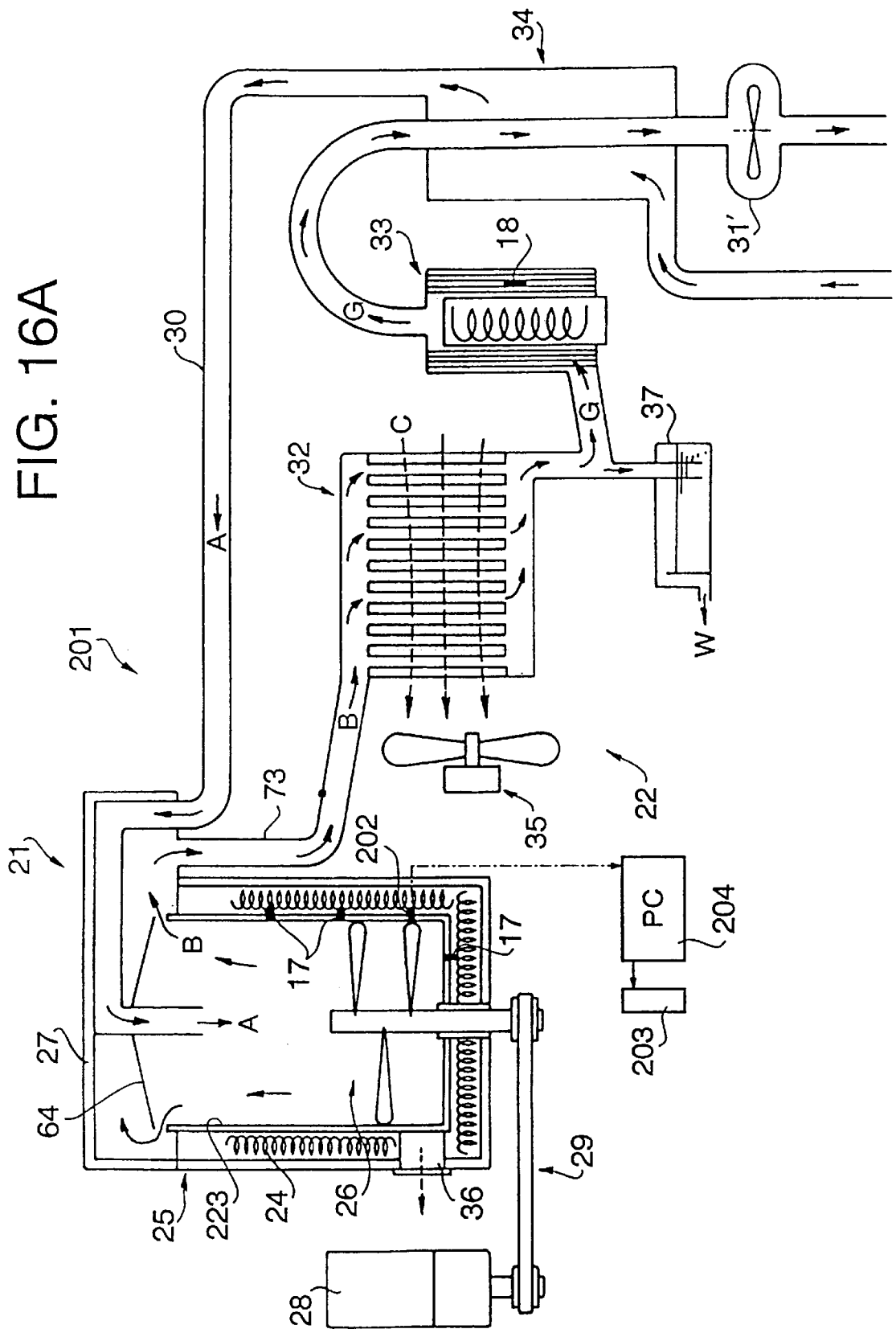
FIG. 16A illustrates a modification of the garbage processing apparatus of the second embodiment.

Various modifications and changes may be made to this particular embodiment. For instance, the steam B is taken out by the high pressure fresh air A supplied by the blower 31 in the embodiment. However, the steam B may be drawn by a suction device. This structure is schematically illustrated in FIG. 16A. Specifically, a blower 31' is provided to pull the steam B out of the apparatus. In FIG. 16A, the blower 31 is dispensed with. It should be noted, however, that both the blowers 31 and 31' may be provided in the same apparatus. In addition, the steam separator may be cooled by water. The deodorant heater and the heat exchanger may be integrated.

Figure 15:
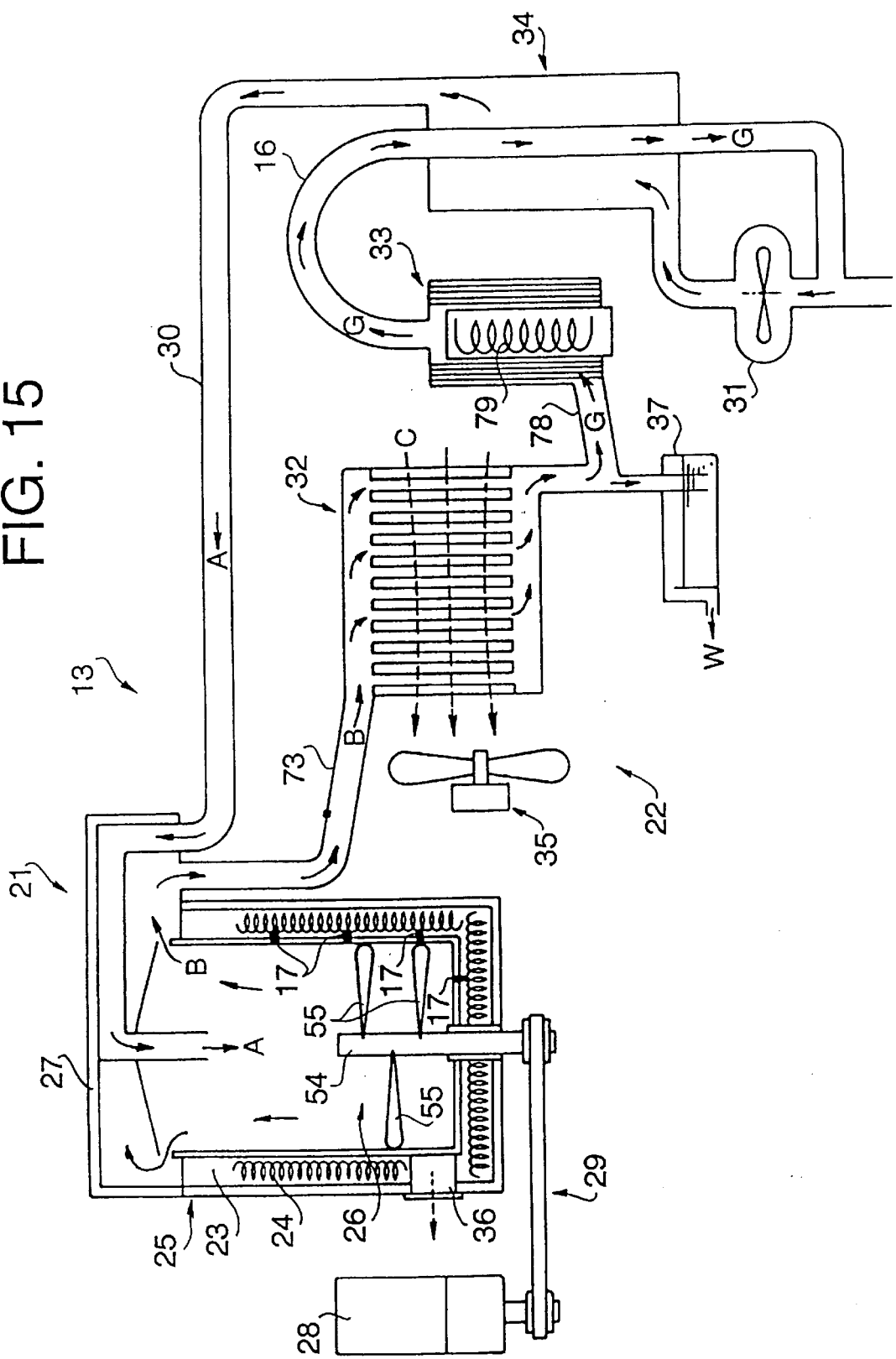
FIG. 15 illustrates a modification of the garbage processing apparatus.

FIG. 15 also illustrates one modification of the first embodiment.

In this modification, a recirculation pipe 16 is provided for recirculating the gas G to the inlet of the blower 31 after the gas G flows through the heat exchanger 34. In short, the pipe 81 shown in FIG. 4 is replaced with the recirculation pipe 16. The recirculation pipe 16 extends from the outlet of the deodorant heater 33. After passing through the heat exchanger 34, the gas G reenters the air pipe 30, the heating vessel 25, the condenser 32, the deodorant heater 33 and the heat exchanger 34 in turn.

The gas G is cooled as it passes through the heat exchanger 34 so that the blower 31 is not subjected to a hot gas and the longevity of the blower 31 is not shortened by this recirculation. On the other hand, the gas G has a higher temperature than the ambient air A even after passing through the heat exchanger 34. Therefore, by recirculating the gas G, the temperature of the fresh air entering the heating vessel 25 is further raised than the arrangement 12 shown in FIG. 4. Accordingly, the power supply to the heater coil 24 is more saved.

In addition, the gas G contains an odorant substance more-or less when it is discharged from the pipe 81 in the embodiment shown in FIG. 4. In this arrangement 13, however, the gas G is not discharged to the environment but recirculated to the heating vessel 25 and undergoes the deodorant process repeatedly. Therefore, it is possible to completely deodorize the gas G.

When the drying operation is completed, the heating device 21 may be deactivated and the deodorant device 22 is only activated for a prescribed period for recirculation of the gas G.

It should be noted that part of the gas G may be recirculated to the inlet of the blower 31 and the remainder may be discharged to the environment. It should also be noted that the gas G may be recirculated to the exit of the blower 31.

Second Embodiment:

A second embodiment of the present invention will be described with reference to FIGS. 16 to 21.

A garbage processing apparatus 201 of this embodiment is similar to that shown in FIGS. 1 to 14 so that like numerals are assigned to like parts and their description will be omitted.

This garbage processing apparatus 201 further includes a temperature sensor 202 for detecting a temperature T of an inner wall 223 of the heating vessel 25 and a controller 204 for controlling actuation units (collectively represented by the block 203) of various parts including the heater 24 based on a detection value of the temperature sensor 202. The controller 204 is turned on by an operator.

The temperature sensor 202 is buried in the inner wall 223 near the bottom of the heating vessel 25. Preferably, this position of the temperature sensor 202 is a position at which the garbage still contacts the inner wall 223 over the sensor 202 even after the garbage volume is reduced upon heating and drying of the garbage. The inner wall 223 has a predetermined thickness and is made from casting (e.g., casting iron or aluminum alloy). The outer surface of the inner wall 223 is covered with a heat insulator (not shown). The heater 24 surrounds the inner wall 223 and an outer wall of the vessel 25 surrounds the heater 24. The outer wall is made from a metal plate such as a stainless plate.

Figure 17:
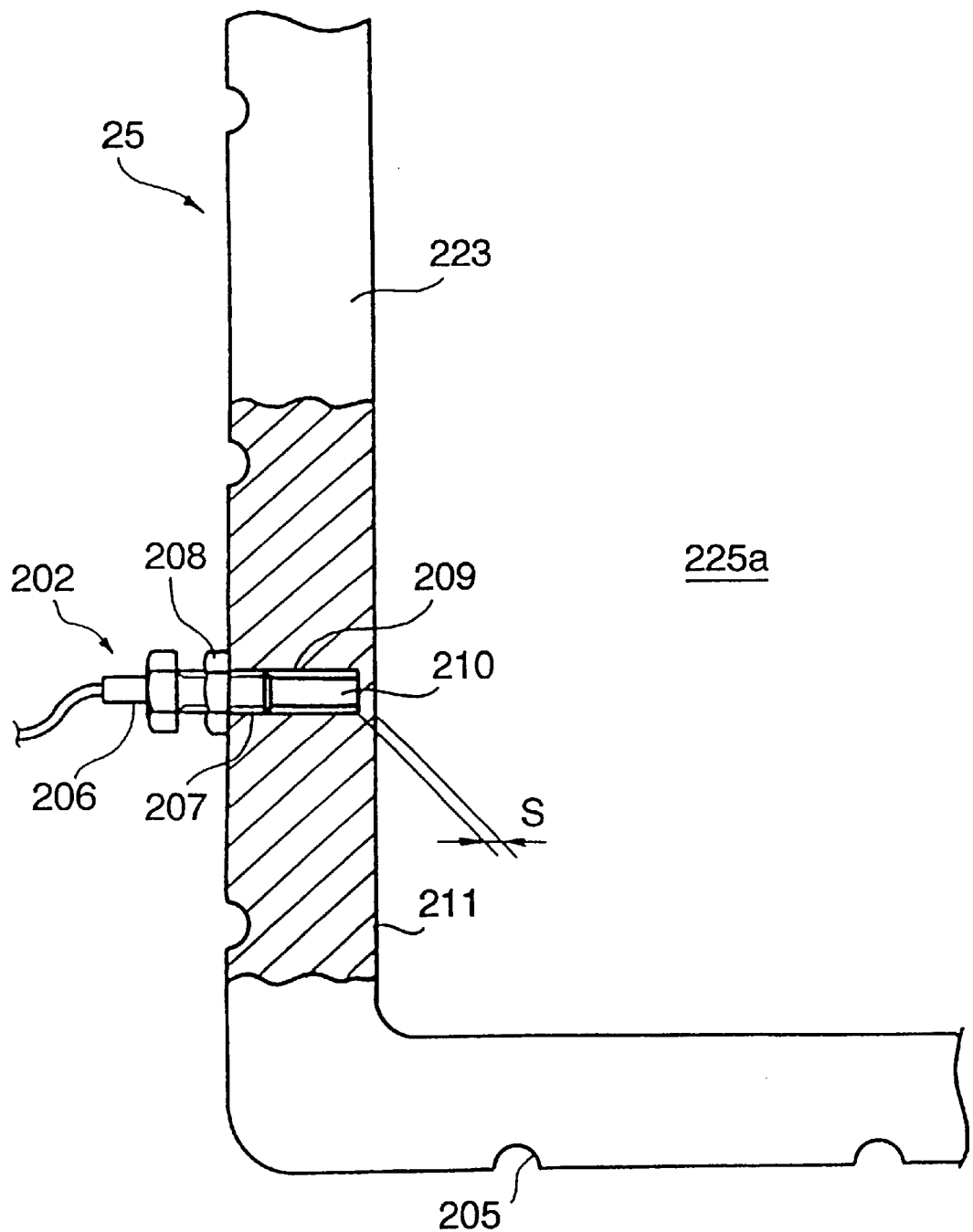
FIG. 17 is an enlarged cross section of a wall of a heating vessel of the garbage processing apparatus shown in FIG. 16 together with a temperature sensor buried in the wall.

Referring to FIG. 17, a plurality of grooves 205 is formed in the outer surface of the inner wall 223 for installation of a sheathed heater (not illustrated for clarification). The sheathed heater is the heater 24 in this embodiment. It should be noted that the heater 24 is not limited to the sheathed heater, but any type of suitable heater may be employed as long as it can dry the garbage.

The temperature sensor 202 includes a main body 206 having a threaded portion 207 and a lock nut 208 engaged over the thread 207. The temperature sensor 202 is threaded into a bore 209 drilled from the outer surface of the inner wall 223 toward the center of the heating vessel 25 and secured by the nut 208. The sensor main body 206 also has a heat sensitive portion 210 which is directed toward the interior 225a of the heating vessel 25. The depth of the bore 209 is slightly smaller than the thickness of the inner wall 223. Specifically, the end of the bore 209 is distanced from the inner surface 211 of the inner wall 223 by "S" (e.g., several mm or 2 to 9 mm). Therefore, the temperature sensor 202 measures the inner wall temperature T which is substantially equal to the temperature of the interior 225a of the heating vessel 25. The controller 204 controls the heater 24 for heating the garbage in the vessel 25, the motor 28 for actuating the stirring device 26, the blower 31 for feeding the fresh air A into the heating vessel 25, the deodorant heater 33 for removing the smell from the gas G and the cooling fan 35 for cooling the condenser 32 by the ambient air C. When the drying operation in the heating vessel 25 proceeds and the temperature T of the inner wall 223 of the vessel 25 detected by the sensor 202 reaches a prescribed value T1, the controller 204 automatically deactivates the motor 28, the blower 31, the deodorant heater 33 and the cooling fan 35.

Figure 18:
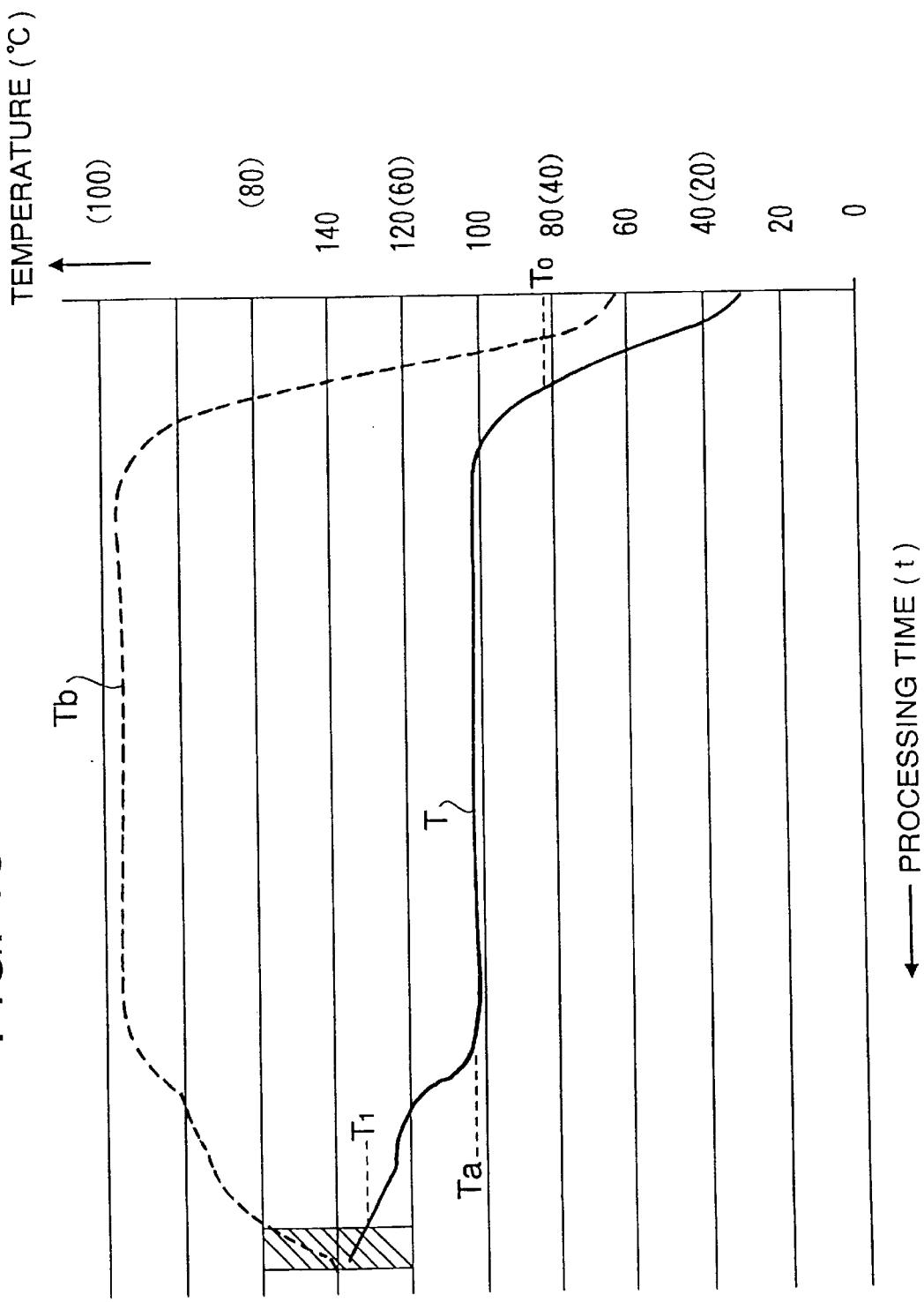
FIG. 18 depicts a temperature curve of the heating vessel wall and that of a steam generated in the heating vessel.

The temperature profile of the inner wall 223 obtained through experiments is illustrated in FIG. 18. As shown, the inner wall temperature T (solid line) rises steeply from the beginning of the drying operation. This indicates the temperature rising process of the garbage thrown into the heating vessel 25. The garbage gains Joule heat from the heater 24. As the time t passes by, the inner wall temperature T stabilizes at a stationary value Ta about 100° C. This indicates lively vaporization of the moisture in the garbage. All the Joule heat from the heater 24 is consumed for vaporization. Then, the inner wall temperature T gradually increases from a certain point. This indicates that the moisture content is considerably reduced and the dried solid substance raises its temperature. When the inner wall temperature T reached a shaded range, the inventors examined the garbage condition and found that the water content was 10 to 15% and the garbage was reduced to a volume suitable for handling. Accordingly, this temperature (e.g., 135 ° C.) is selected as the operation termination temperature T1. The controller 204 deactivates the motor 28, the blower 31, the deodorant heater 33 and the cooling fan 35 when the inner wall temperature T detected by the temperature sensor 202 reaches Ti. FIG. 18 also illustrates the temperature Tb of the steam B by the broken line curve. Its scale is shown in parentheses. The steam temperature Tb also rises steeply in an initial period and then stabilizes at a certain temperature like the inner wall temperature T. However, the steam temperature Tb drops when the inner wall temperature T rises again. It is assumed that this indicates that the amount of steam decreases as the drying proceeds, and therefore the steam temperature Tb is influenced by the incoming fresh air A fed into the heating vessel 25. Whatever the reasons is, the inner wall temperature T represents the drying condition of the garbage in the heating vessel 25 (or the steam generation in the heating vessel).

Referring back to FIG. 16, the garbage processing apparatus 201 of this embodiment also includes a set of temperature sensors 17 for detecting the temperature of the drying heater 24 and another temperature sensor 18 for detecting the temperature of the deodorizing heater 33. These heater sensors 17 and 18 are provided for maintaining the heaters 24 and 33 at predetermined temperatures respectively (e.g., the heater 24 is at 100 to 125° C. and the heater 33 is at 500 to 600° C.). When a temperature detected by the sensor is not in the predetermined temperature range, the controller 204 regulates the heater (will be described in detail later).

Next, the control performed by the controller 204 will be described with reference to FIGS. 19 and 20.

Figure 19:
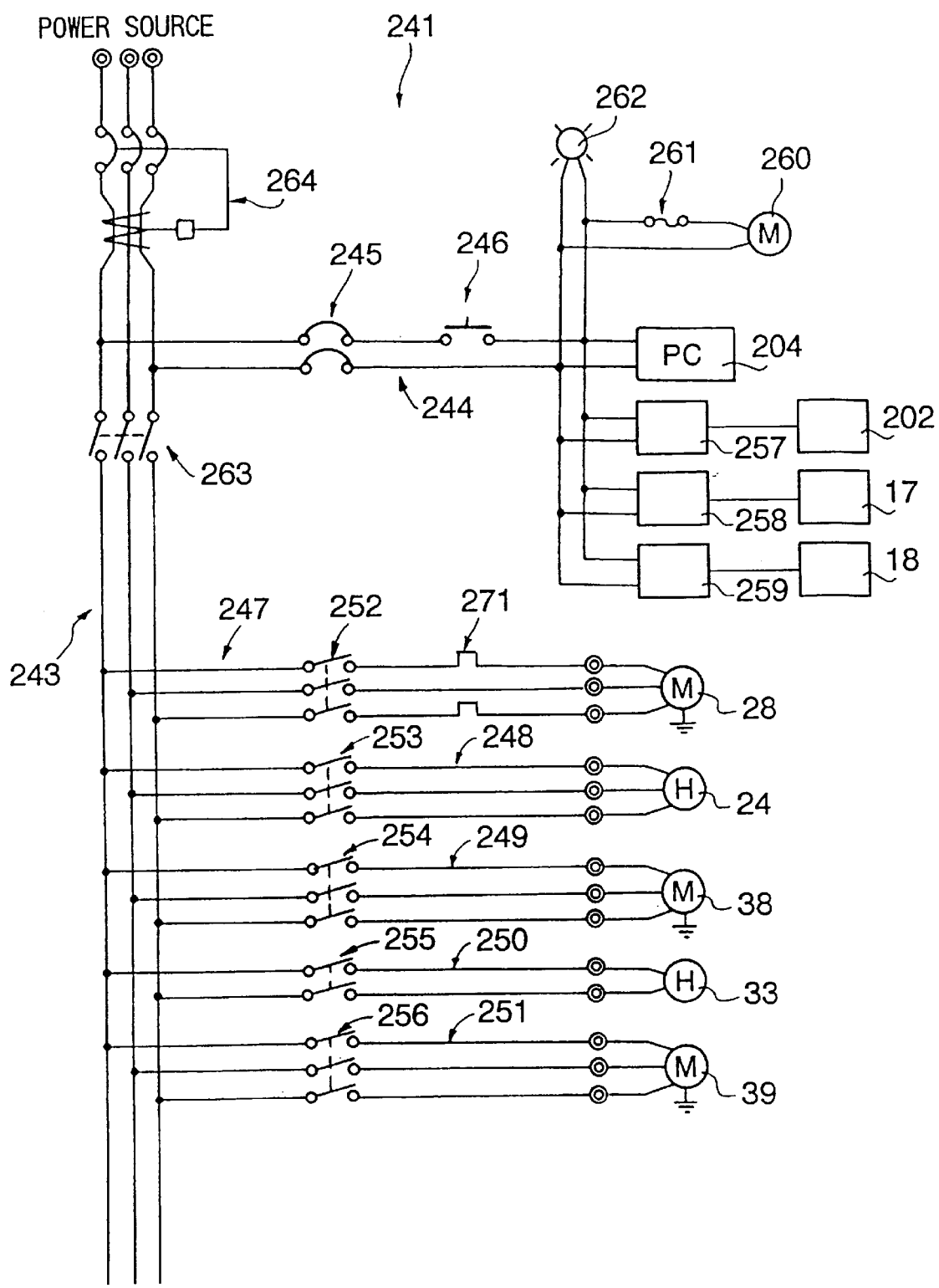
FIG. 19 diagrammatically illustrates a current consuming circuitry controlled by a controller of the apparatus shown in FIG. 16.
Figure 20:
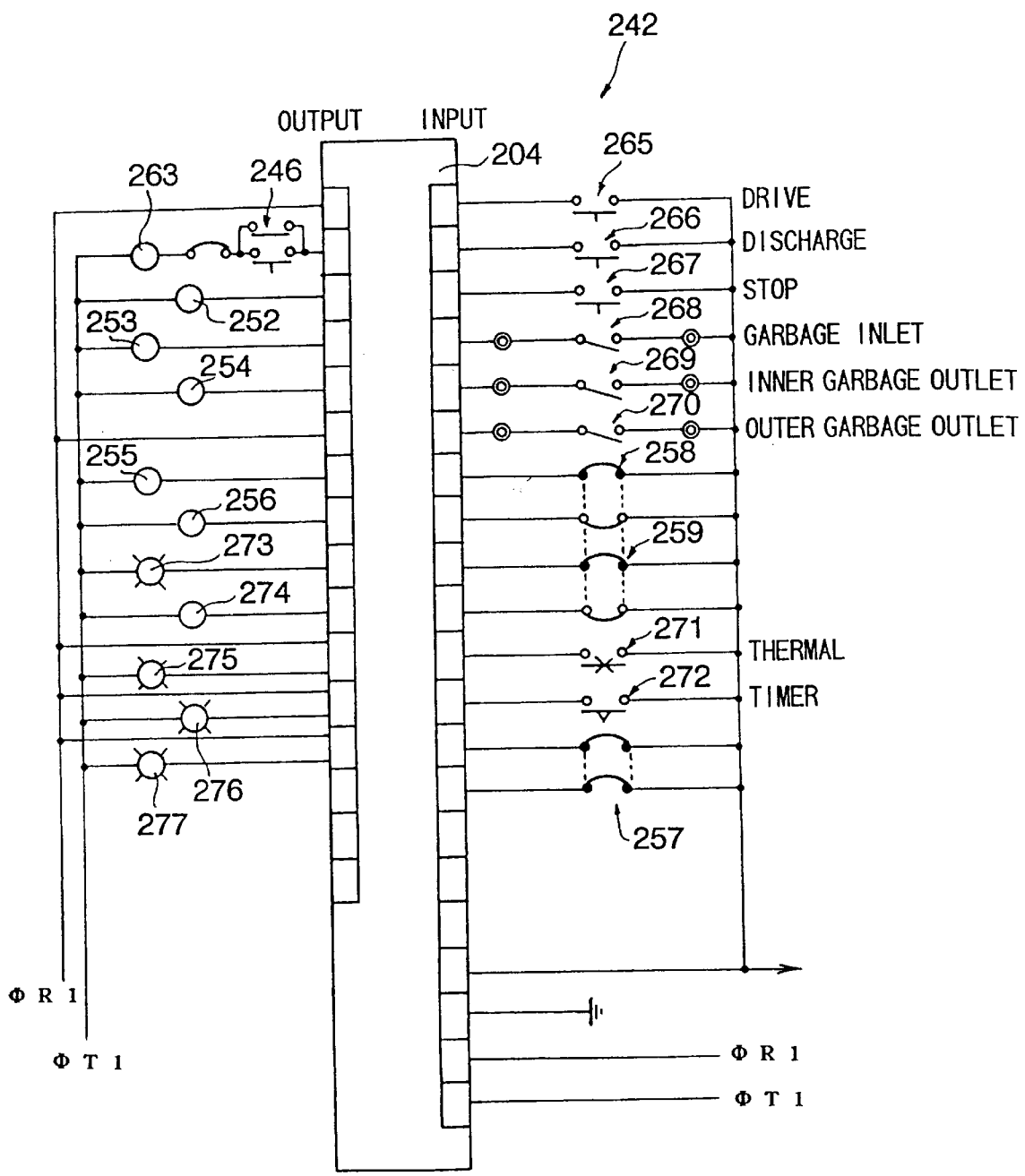
FIG. 20 also diagrammatically illustrates a control circuitry of the garbage processing apparatus shown in FIG. 16.

The controller 204 is equipped with a current consuming circuit 241 and a control circuit 242 for controlling operations of various parts of the apparatus as shown in FIGS. 19 and 20.

Referring first to FIG. 19, the current consuming (or electric load) circuit 241 includes the motor 28 of the stirring device 26, the drying heater 24, a motor 38 of the cooling fan 35, the deodorant heater 33 and a motor 39 of the blower 31, all of which are connected in parallel to the controller 204. In this current consuming circuit 241, a main circuit 243 is connected with a power source, and a branch circuit 244 extends to the controller 204 from the main circuit 243. The branch circuit 244 includes a breaker 245 and a key switch 246. Temperature regulators 257 to 259 are coupled in parallel to the branch circuit 244. These temperature regulators 257 to 259 are also coupled to the temperature sensor 202 provided in the inner wall 223 of the heating vessel 25, the temperature sensors 17 of the heater 24 and the temperature sensor 18 of the deodorant heater 33 respectively. If the temperature detected by the sensor 17/18 is not in the prescribed temperature range, the associated temperature regulator 258/259 sends a signal current indicative of such a situation to the controller 204 so that the controller 204 turns on/off the electromagnetic relay 253/255. If the temperature is below the predetermined range, the relay is brought into a connecting position to feed the electric power to the heater. If the temperature is over the predetermined range, the relay is moved to a disconnecting position to feed no electricity to the heater.

A motor 260 for activating a cooling fan (not shown) to cool the control devices including the control 204 and an associated fuse 261 are also connected with the branch circuit 244. A first lamp 262 also connects to the branch circuit 244 to indicate an on condition of the key switch 246.

Current consuming circuits 247 to 251 which have the motor 28, the heater 24, the motor 38, the heater 33 and the motor 39 at their ends respectively also extend from the main circuit 243 in parallel. These current consuming circuits 247 to 251 include electromagnet relays 252 to 256 respectively which are activated by signals outputted from the controller 204.

The main circuit 243 also includes a main electromagnetic relay 263 which is turned on and off according to the key switch 246. The main electromagnetic relay 263 is located between the branch circuit 244 and the current consuming circuits 247 to 251. An earth leakage breaker 264 is provided between the power source and the branch circuit 244. A reference numeral 271 near the electromagnetic relay 252 designates a thermal (will be described later in detail).

Referring to FIG. 20, the control circuit 242 has an operation (or start) button 265 for starting the process, a garbage discharge button 266, a stop button 267 for deactivating the apparatus, a first limit switch 268 provided on the lid 27 of the vessel 25, a second limit switch 269 provided on the inner discharge door 101 at the discharge opening 36 (FIG. 9) and a third limit switch 270 provided on the outer discharge doors 50 (FIG. 10), all of which are connected to the input of the controller 204. The buttons 265 to 267 are provided in an operation panel (not shown). Further, the temperature regulators 257 to 259, the thermal 271 for detecting an excessive load condition of the stirring device 26 and a timer 272 as a backup element for automatic deactivation are connected to the input of the controller 204. To the output of the controller 204, connected are the key switch 246, the electromagnetic relays 252 to 256 and 263, a second lamp 273 for indicating an excessive load condition, a buzzer 274 for also indicating the same excessive load condition, a third lamp 275 for indicating a condition of the timer 272, a fourth lamp 276 for indicating a running condition and a fifth lamp 277 for indicating a discharge condition.

Figure 21:
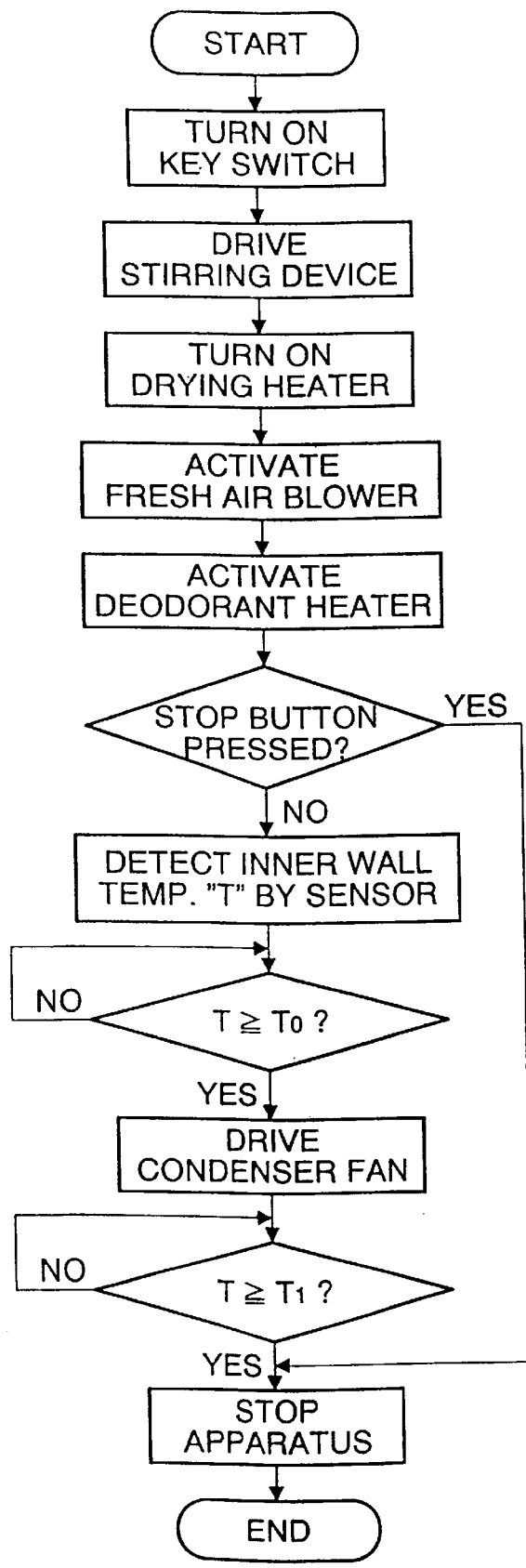
FIG. 21 is a flowchart showing a series of operations performed in a garbage drying process.

Referring to FIG. 21, the garbage processing process will be described.

First, the lid 27 is opened by the operator and the garbage which may have been squeezed to manually reduce a moisture content from the garbage is fed into the drying vessel 25 by the operator. Then, the lid 27 is closed and the key switch 246 is turned on to activate the controller 204. At the same time, the operation button 265 is depressed. As a result, the lamp 276 is lightened for indicating that the apparatus 201 is in a drive condition. Simultaneously, the cooling fan for the controls is turned on, and the motor 28 is actuated to drive the stirring device 26. If there is no abnormal condition at this point such as an excessive load on the stirring device, the heater 24 is turned on to raise the temperature of the drying vessel 25. Specifically, the electricity is supplied to the heater 24 so that the Joule heat heats and dries the garbage while the garbage is crushed and stirred by the stirring device 26. Crushing and stirring the garbage promotes the vaporization of the moisture from the garbage. If there is still no abnormal condition such as excessive temperature elevation in the vessel 25, the motor 39 of the blower 31 and the deodorant heater 33 are turned on so that the high pressure fresh air A is introduced into the vessel 25 to force the steam B out of the vessel 25. The steam B then flows into the condenser 32 through the pipe 73 so that it is separated into the gas G and the condensed water W. The water W is discharged from the condenser 32 from the lower drain pipe. The gas G, on the other hand, is heated by the deodorant heater 33 so that it is oxidized and deodorized. After that, the gas G transfers its heat to the fresh air A in the heat exchanger 34 before it is expelled to the atmosphere. The heaters 24 and 33 are maintained in the respective predetermined temperature ranges under control of the controller 204.

It should be noted here that the gas G may be recirculated to the fresh air pipe 30 or the inlet of the blower 31 as illustrated in FIG. 15.

When the temperature of the vessel inner wall 223 rises to a first predetermined value To (e.g., 80° C.), the temperature sensor 202 sends a signal to the controller 204 to activate the cooling fan 35 of the condenser 32 for promotion of gas/water separation. As the garbage drying process proceeds and the sensor 202 determines that the inner wall temperature T reaches a second predetermined value T1, then such a detection signal is sent to the controller 204 so that the apparatus 201 is brought into the deactivation mode. Specifically, the controller 204 stops the motor 28 and the heater 24 so that no further garbage stirring and heating is carried out. Further, the motors 38 and 39 and the heater 33 of the deodorant unit 22 are turned off so that the air blowing and gas deodorization are stopped. At this point, the garbage is significantly reduced in volume, e.g., to about one tenth as compared with the garbage of before the drying operation. Thus, the garbage now contains a very small amount of moisture and therefore it is easy to handle. Then, the operator opens the outlet 36 of the vessel 25 and takes the garbage out. If the operator notices an abnormal condition, for instance, and pushes the stop button during the drying and deodorizing process, the apparatus 201 is manually deactivated.

As described above, the inventors found that the temperature T of the inner wall 223 of the vessel 25 correspondingly changes with the drying condition of the garbage in the vessel 25. In this invention, therefore, when the temperature sensor 202 buried in the inner wall 223 indicates the predetermined value T1, the controller 204 determines that the garbage is sufficiently dried in the vessel 25. Consequently, the controller 204 turns off the various parts of the apparatus 201 including the stirring device 26 and the heater 24. Therefore, a wasteful operation of the apparatus 201 can be avoided.

It should be noted that the teaching of the present invention is applicable to any type of apparatus having a heating device.

What is claimed is:
1. An apparatus for processing garbage comprising:
   a vessel for receiving the garbage, the vessel having a wall with outside and inside surfaces;
   means for crushing and stirring the garbage in the vessel;
   means located outwardly of the outside surface of the vessel wall for heating the wall of the vessel so as to heat and dry the garbage in the vessel;
   a blower for introducing an ambient air into the vessel to discharge a steam generated upon heating and drying of the garbage out of the vessel;
   said wall having a bore extending inwardly from the outside surface of the wall to an inner end surface of the bore located closer to the inside surface of the wall than to the outside surface of the wall;

a temperature sensor having a heat sensitive portion located in said bore and engaged with the inner end surface of the bore for detecting a temperature of the wall of the vessel at the inner end surface of the bore; and a controller for at least deactivating the heating means when the detected temperature exceeds a prescribed value.

2. The apparatus of claim 1, wherein the prescribed value is about 135° C.

3. A method of controlling a garbage processing device, the garbage processing device having a vessel for receiving the garbage, the vessel having a wall with outside and inside surfaces, means for crushing and stirring the garbage in the vessel, a heater located outwardly of the outside surface of the vessel wall for heating the wall of the vessel so as to heat and dry the garbage in the vessel, and a blower for introducing an ambient air into the vessel to discharge a steam generated upon heating and drying of the garbage out of the vessel, comprising the steps of:

A) detecting a temperature of the wall of the vessel at the end surface of a bore in the wall which bore end surface is located closer to the inside surface of the wall than to the outside surface of the wall; and B) at least deactivating the heater when the detected temperature exceeds a prescribed value.

4. The method of claim 3, wherein the prescribed value is about 135° C.

5. The apparatus of claim 1, wherein said steam is an odorous and corrosive steam generated from the garbage, the blower introduces the ambient air in a pressurized condition into the vessel to force said odorous and corrosive steam generated upon heating and drying of the garbage out of the vessel without said blower being subjected to said steam, and said apparatus further comprises:

an air-cooled odorous and corrosive steam separator for separating the odorous and corrosive steam into a water and a gas, deodorant means located downstream of the odorous and corrosive steam separator for deodorizing the gas emanating, from the odorous and corrosive steam separator by heating and oxidizing the gas, and a heat exchanger located downstream of the deodorant means for heating the ambient air using the gas heated by the deodorant means before the ambient air is introduced into the vessel.

6. The apparatus of claim 1, wherein said steam is an odorous and corrosive steam generated from the garbage, the blower introduces an ambient air in a pressurized condition into the vessel to force said odorous and corrosive steam generated upon heating and drying of the garbage out of the vessel without said blower being subjected to said steam, and said apparatus further comprises:

an air-cooled odorous and corrosive steam separator for separating the odorous and corrosive steam into a water and gas;

first deodorant means located downstream of the odorous and corrosive steam separator for deodorizing the gas emanating from the odorous and corrosive steam separator by heating and oxidizing the gas; and a second deodorizing means located downstream of the odorous and corrosive steam separator for deodorizing the water emanating from the odorous and corrosive steam separator.

7. The apparatus of claim 1, wherein said steam is an odorous and corrosive steam generated from the garbage, said vessel has a vertical axis in its height direction, the vessel having a garbage inlet opening at its top and a peripheral wall;

said means for crushing and stirring the garbage in the vessel includes a rotary device placed in the vessel, an axis of rotation of the rotary device being coaxial to the vertical axis of the vessel, said blower introduces an ambient air in a pressurized condition into the vessel to force said odorous and corrosive steam generated upon heating and drying of the garbage out of the vessel without said blower being subjected to said odorous and corrosive steam, and said apparatus further comprises:

drive means located next to the peripheral wall of the vessel for driving the rotary device;

transmission means for transmitting a drive power from the drive means to the rotary device; and deodorant means for deodorizing an odorous and corrosive steam generated upon heating and drying of the garbage after the odorous and corrosive steam is expelled out of the vessel, and wherein the deodorant means extends vertically next to the garbage heating and drying means;

wherein the deodorant means includes means for separating the odorous and corrosive steam into a gas and water and a cooling fan for producing a flow of air which cools the odorous and corrosive steam separating means;

wherein said deodorant means includes vertically extending second heating means located downstream of the odorous and corrosive steam separating means for deodorizing the gas discharged from the odorous and corrosive steam separating means by heating and oxidizing the gas; and wherein said deodorant means further includes a means located downstream of the odorous and corrosive steam separating means for deodorizing the water discharged from the odorous and corrosive steam separating means.

8. The apparatus of claim 1 wherein said steam is an odorous and corrosive steam generated from the garbage, the blower pressurizes an ambient air and feeds it into the vessel to discharge the odorous and corrosive steam from the vessel without said blower being subjected to said odorous and corrosive steam, the blower having an inlet, and said apparatus further comprises:

a steam separator for separating the odorous and corrosive steam into a water and a gas;

second heating means provided downstream of the odorous and corrosive steam separator for heating and oxidizing the gas emanating from the odorous and corrosive steam separator to reduce a smell of the gas;

a heat exchanger placed downstream of the second heating means for heating the ambient air by the gas heated by the second heating means before the ambient air is introduced into the vessel, the heat exchanger having an outlet; and a recirculation passage for connecting the outlet of the heat exchanger to the inlet of the blower.

9. The apparatus of claim 8, wherein the odorous and corrosive steam separator is a condenser.

10. The method of claim 3 wherein the steam generated from the heater for heating and drying the garbage in the vessel is an odorous and corrosive steam and wherein the method includes the further steps of:

C) feeding an ambient air by means of the blower into the vessel for discharging the odorous and corrosive steam generated upon heating and drying of the garbage out of the vessel without said blower being subjected to said odorous and corrosive steam;

D) separating the discharged odorous and corrosive steam into a water and a gas;

E) heating and oxidizing the gas so as to deodorize the gas using a second heater, and F) heating the ambient air using the gas heated by the second heater before the ambient air is fed into the vessel.

11. The method of claim 3, wherein the steam generated from the heater for heating and drying the garbage in the vessel is an odorous and corrosive steam and wherein the method includes the further steps of:

C) feeding an ambient air by means of the blower into the vessel for discharging the odorous and corrosive steam generated upon heating and drying of the garbage out of the vessel without said blower being subjected to said odorous and corrosive steam;

D) separating the discharged odorous and corrosive steam into a water and a gas;

E) heating and oxidizing the gas so as to deodorize the gas using a second heater;

F) storing the water in a tank after step D); and

G) immersing a deodorant agent in the tank before step F).

12. The apparatus of claim 7, wherein:

said means located downstream of the odorous and corrosive steam separating means includes a tank for storing the water discharged from the odorous and corrosive steam separating means; and wherein said tank for storing the water discharged from the odorous and corrosive steam separating means contains a deodorant agent placed into said tank.

13. The apparatus of claim 1, wherein the temperature sensor is located in the vessel wall at a position such that the vessel wall in the vicinity of the temperature sensor still contacts the garbage even after the heating and drying of the garbage is finished.

* * * * *